United States Patent [19]

McGuckin et al.

[11] 4,374,194
[45] Feb. 15, 1983

[54] DYE IMBIBITION PHOTOHARDENABLE IMAGING MATERIAL AND PROCESS FOR FORMING POSITIVE DYE IMAGES

[75] Inventors: Hugh G. McGuckin; Susan E. Hartman; Donald P. Specht, all of Rochester, N.Y.

[73] Assignee: Eastman Kodak Company, Rochester, N.Y.

[21] Appl. No.: 327,527

[22] Filed: Dec. 4, 1981

Related U.S. Application Data

[63] Continuation-in-part of Ser. No. 214,144, Dec. 8, 1980, abandoned.

[51] Int. Cl.³ .............. G03C 5/54; G03C 1/40; G03C 5/00; B41M 5/00
[52] U.S. Cl. .................... 430/199; 430/271; 430/285; 430/941; 430/308; 101/464; 428/480; 428/483
[58] Field of Search ............. 430/199, 308, 271, 285, 430/324, 941; 101/464; 428/480, 483

[56] References Cited

U.S. PATENT DOCUMENTS

| | | | |
|---|---|---|---|
| 3,173,787 | 3/1965 | Clement et al. | 96/35 |
| 3,488,706 | 1/1970 | Cohen et al. | 96/29 |
| 3,557,066 | 1/1971 | Cohen et al. | 260/78.5 |
| 3,625,694 | 12/1971 | Cohen et al. | 96/84 |
| 3,709,690 | 1/1973 | Cohen et al. | 96/67 |
| 3,758,445 | 9/1973 | Cohen et al. | 260/78 |
| 3,770,439 | 11/1973 | Taylor | 96/77 |
| 3,773,509 | 11/1973 | Ohyama et al. | 96/57 |
| 3,859,096 | 1/1975 | Burness et al. | 96/84 |
| 3,898,088 | 8/1975 | Cohen et al. | 96/84 |
| 3,929,489 | 12/1975 | Arcesi et al. | 96/115 |
| 3,944,424 | 3/1976 | Cohen et al. | 96/119 |
| 3,958,995 | 5/1976 | Campbell et al. | 96/84 |
| 4,147,552 | 4/1979 | Specht et al. | 96/115 |
| 4,202,785 | 5/1980 | Merrill et al. | 430/106 |
| 4,204,866 | 5/1980 | Horak et al. | 430/306 |
| 4,220,700 | 9/1980 | McGuckin et al. | 430/143 |

FOREIGN PATENT DOCUMENTS

| | | |
|---|---|---|
| 1245952 | 9/1971 | United Kingdom. |
| 1261925 | 1/1972 | United Kingdom. |
| 1470059 | 4/1977 | United Kingdom. |

OTHER PUBLICATIONS

Research Disclosure, Apr. 1981, Item No. 20437.
Research Disclosure, May 1978, Item No. 16976.
Research Disclosure, Dec. 1978, Item No. 17643.
Research Disclosure, May 1977, Item No. 15705.

*Primary Examiner*—Richard L. Schilling
*Attorney, Agent, or Firm*—Richard E. Knapp

[57] ABSTRACT

A positive, continuous tone, dye image is produced by means of a dye imbibition imaging element comprising (a) a support having thereon, (b) a cationic mordant layer for an anionic dye, and (c) a sensitized photohardenable photopolymer layer consisting essentially of a photosensitive polyesterionomer. A process for forming a positive, continuous tone dye image in a dye imbibition imaging element, as described, comprises the steps of: (1) imagewise exposing the photopolymer layer of the element to activating radiation to imagewise harden the photopolymer layer; then (2) developing the photopolymer layer by means of water rinsing; and, then (3) imbibing an anionic dye into the mordant layer through the unexposed areas of the photopolymer layer. Alternatively, the process comprises immersing the imagewise-exposed element from step (1) into a bath comprising the anionic dye without the need for a water rinsing step. This alternative process enables the anionic dye to be imbibed into the mordant layer through the unexposed areas of the photopolymer layer without the need for removing a portion of the unexposed areas of the photopolymer layer. The anionic dye is optionally transferable into another mordant layer.

26 Claims, 8 Drawing Figures (IMAGEWISE EXPOSE)

DEVELOPMENT BY WATER AND IMBIBE ANIONIC DYE (DYE IMBIBED)

(DYE IMBIBED WITHOUT DEVELOPMENT)

DYE IMBIBITION PHOTOHARDENABLE IMAGING MATERIAL AND PROCESS FOR FORMING POSITIVE DYE IMAGES

This is a continuation-in-part patent application of U.S. Ser. No. 214,144 of Hugh G. McGuckin et al, filed Dec. 8, 1980, now abandoned, entitled "Dye Imbibition Photohardenable Imaging Material and Process for Forming Positive Dye Images".

BACKGROUND OF THE INVENTION

1. Field of the Invention

This invention relates to a dye imbibition imaging element comprising a photosensitive polyesterionomer for forming a positive, continuous tone, dye image. It also relates to a process for forming such a dye image by means of water rinsing the imaging element after imagewise exposure and imbibing an anionic dye into the element.

2. State of the Art

Photohardenable imaging compositions and elements useful in preparing continuous tone dye images, such as for color proofing, are known. These are described in, for example, *Research Disclosure*, May 1978, Item No. 16976, and U.S. Pat. No. 4,220,700. The known compositions and elements involve a wash-off light-sensitive composition comprising, in admixture, as a photohardenable material, a light-sensitive diazo resin and a mordant for an anionic dye. Such a composition is useful for forming a dye image by imagewise exposing the composition as a layer on a suitable support, then developing the layer by means of water by rinsing, followed by imbibing an anionic dye into the layer in which it is immobilized by the mordant. The dye image is capable of being transferred to a receiver layer comprising a cationic mordant of greater mordanting strength than the mordant mixed with the light-sensitive diazo resin. While such photohardenable imaging compositions and elements are useful for forming negative dye images, a need has existed for a suitable photohardenable, dye imbibition imaging element for producing a positive, continuous tone, dye image.

The photohardenable imaging materials designed to produce high contrast images, such as by means of a photoresist, are not useful for forming continuous tone, dye images. In this regard, uncharged photopolymers, such as poly[1,4-cyclohexylenebis(oxyethylene) succinate-co-p-phenylenebis(acrylate)] (45:55), provide higher contrast images than are desired for positive, continuous tone, dye images. This is illustrated in the following comparative examples.

SUMMARY OF THE INVENTION

According to the invention, a positive, continuous tone, dye image is produced by means of a dye imbibition imaging element comprising, in sequence:
 (a) a support having thereon
 (b) a cationic mordant layer for an anionic dye, and
 (c) a sensitized photohardenable photopolymer layer.
The photohardenable photopolymer layer consists essentially of a photosensitive polyesterionomer, preferably a photosensitive polyesterionomer A represented by the formula:

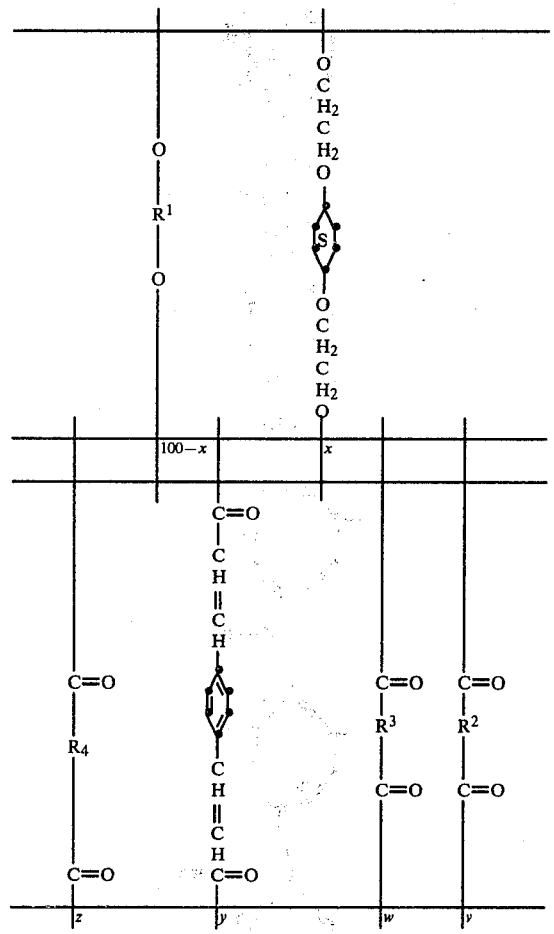

wherein:

$R^1$ is straight or branched chain alkylene containing 2 to 10 carbon atoms, such as ethylene, propylene, butylene, trimethylene, 2,2-dimethyl-1,3-propylene or 1,10-decylene; a cycloalkylene group containing 5 or 6 carbon atoms, such as 1,4-cyclohexylene or 1,4-cyclohexylenedimethylene; or an aliphatic ether group containing 3 to 12 carbon atoms in the aliphatic ether chain, such as oxydiethylene and ethylenebis(oxyethylene);

$R^2$ is an aromatic group containing 6 to 12 carbon atoms, such as phenylene or naphthylene;

$R^3$ is straight or branched chain alkylene containing 2 to 10 carbon atoms, such as ethylene, propylene, butylene, 2,2-dimethyl-1,3-propylene and 1,10-decylene;

$R^4$ is an ionic group selected from those having the structures:

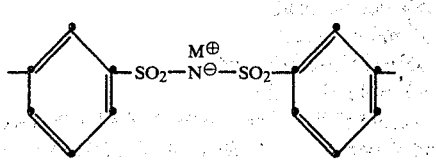

-continued

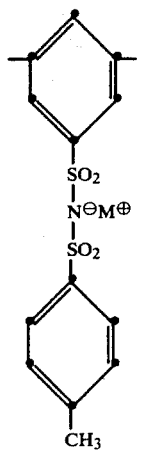

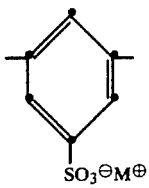

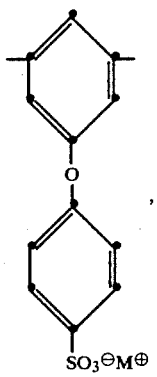, and

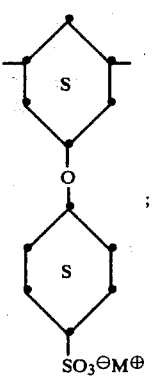;

M+ is an alkali metal or ammonium ion;
x is 50 to 100 mole percent;
v is 0 to 35 mole percent;
w is 0 to 35 mole percent;
y is 50 to 85 mole percent; and
z is 15 to 40 mole percent.

The photosensitive polyesterionomer is in a layer separate from and superposed on the layer comprising the mordant.

A process for forming a positive, continuous tone, dye image in a dye imbibition imaging element, according to the invention, comprises the steps:

(1) imagewise exposing the photopolymer layer of the element to activating radiation to imagewise harden the photopolymer layer;

(2) developing the photopolymer layer by means of water by rinsing; and then, (3) imbibing an anionic dye into the mordant layer through the unexposed areas of the photopolymer layer.

Alternatively, a process for forming a positive, continuous tone, dye image in a dye imbibition imaging element, according to the invention, comprises the steps:

(1) imagewise exposing the photopolymer layer of the element to activating radiation to imagewise harden the photopolymer layer; and, then (2) imbibing at least one anionic dye through the unexposed areas of the photopolymer layer into the cationic mordant layer.

This alternative process avoids the need of removing portions of the photopolymer layer. Imbibing of the anionic dye in the process of the invention is preferably carried out by contacting the element of the invention, after imagewise exposure, with a bath comprising at least one anionic dye in a suitable aqueous solvent, such as water or a mixture of water and a suitable organic solvent. The element is, for example, after imagewise exposure, immersed in a bath comprising at least one anionic dye in a suitable solvent for a sufficient time to enable the desired concentration of dye to be imbibed into the cationic mordant layer.

If desired, a continuous tone, dye image is formed in a receiver layer by a dye transfer process according to the invention. This process for formation of a continuous tone, dye image in a receiver layer comprising a first cationic mordant of a predetermined mordanting strength comprises the steps of:

(a) imagewise exposing a sender element comprising
  (i) a support having thereon:
  (ii) a mordant layer consisting essentially of a second cationic mordant for an anionic dye, the second cationic mordant having a lesser mordanting strength than the first cationic mordant, and having superposed thereon:
  (iii) a sensitized, photohardenable, photopolymer layer consisting essentially of photosensitive polyesterionomer A to imagewise harden the photopolymer layer;

(b) developing the photopolymer layer removing at least part of the unhardened image areas in the photopolymer layer, such as by water rinsing the photopolymer layer;

(c) imbibing at least one anionic dye into the second cationic mordant layer, the dye being temporarily immobilized in the portions of the second cationic mordant corresponding to unexposed portions of the photopolymer layer; and, (d) imagewise transferring the anionic dye to the receiver layer by contacting the receiver layer with the side of the sender element containing the second cationic mordant in the presence of an aqueous solution that aids transfer of the anionic dye into the first cationic mordant.

An alternative process for formation of a continuous tone, dye image in a receiver layer comprising a first cationic mordant of a predetermined mordanting strength comprises the steps:

(a) imagewise exposing a sender element comprising:
   (i) a support having thereon:
   (ii) a mordant layer comprising a second cationic mordant having a lesser mordanting strength than the first cationic mordant, and having superposed thereon:
   (iii) a sensitized, photohardenable, photopolymer layer consisting essentially of photosensitive polyesterionomer A, to imagewise harden the photopolymer layer;
(b) imbibing at least one anionic dye through the unexposed areas of the photopolymer layer into the second cationic mordant layer through unexposed areas of the photopolymer layer without the need of removing portions of the photopolymer layer; and, then
(c) imagewise transferring the anionic dye from the second cationic mordant layer, through the unexposed areas of the photopolymer layer, into the receiver layer containing the first cationic mordant in the presence of an aqueous solution that aids transfer of the anionic dye.

This alternative process also avoids the need of removing portions of the photopolymer layer. Imbibing of the anionic dye in the process into the second cationic mordant is preferably carried out by contacting the element of the invention, after imagewise exposure, with a bath comprising at least one anionic dye in a suitable aqueous solvent, such as water or a mixture of water and a suitable organic solvent.

DESCRIPTION OF THE PREFERRED EMBODIMENTS

The dye imbibition imaging element according to the invention is especially useful as a pre-press color-proofing element for gravure and lithography; however, the element is also useful in other applications in which a positive, continuous tone dye image is desirable, such as the duplication of graphic arts films and microfilm originals. This invention is based, in part, on the discovery that photopolymers that were not thought to be especially useful for formation of continuous tone images could be made useful by preparing and using charged photopolymers as photosensitive polyesterionomers having the described structures.

The photosensitive polyesterionomers are prepared by processes known in the polymer synthesis art. Examples of the preparation of useful photosensitive polyesterionomers are described in, for instance, U.S. Pat. No. 3,929,489 and U.K. Specification No. 1,470,059, the disclosures of which are expressly incorporated herein by reference.

Examples of useful photosensitive polyesterionomers include:

1. poly[1,4-cyclohexylenebis(oxyethylene) succinate-co-p-phenylenebis(acrylate)-co-5-sodiosulfoisophthalate] represented by the formula:

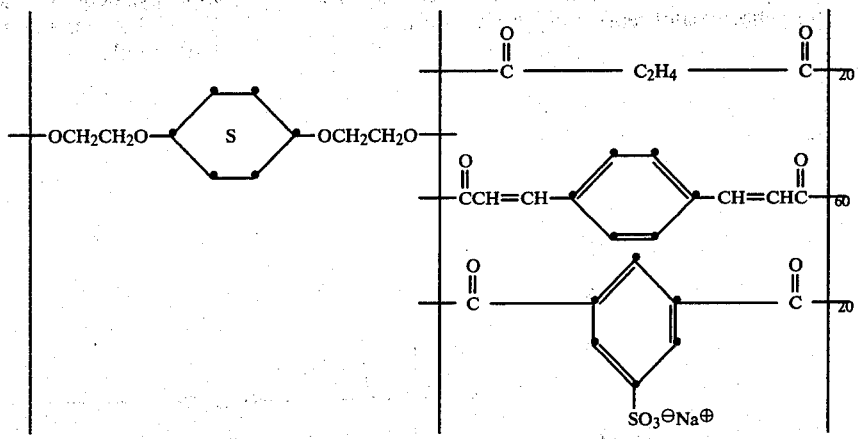

2. poly[1,4-cyclohexylenebis(oxyethylene) succinate-co-p-phenylenebis(acrylate)-co-5-(4-sodiosulfophenoxy)isophthalate] represented by the formula:

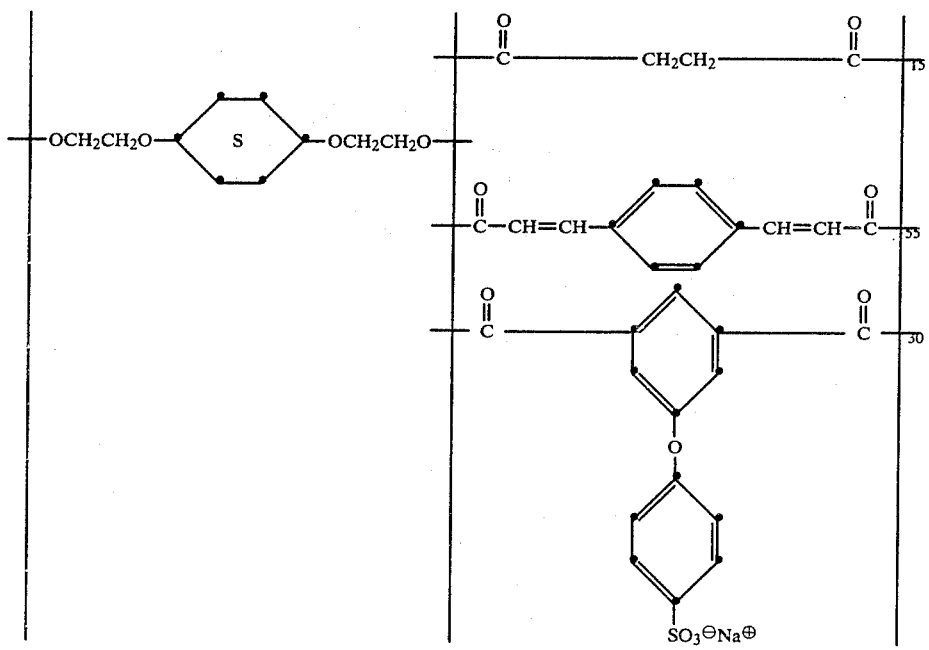
3. poly[1,4-cyclohexylenebis(oxyethylene) succinate-co-p-phenylenebis(acrylate)-co-3,3'-sodioiminodisulfonyldibenzoate] represented by the formula:
4. poly[1,4-cyclohexylenebis(oxyethylene)succinate-co-p-phenylenebis(acrylate)-co-5-(4-sodiosulfocyclohexyloxy)-1,3-cyclohexanedicarboxylate] represented by the formula:
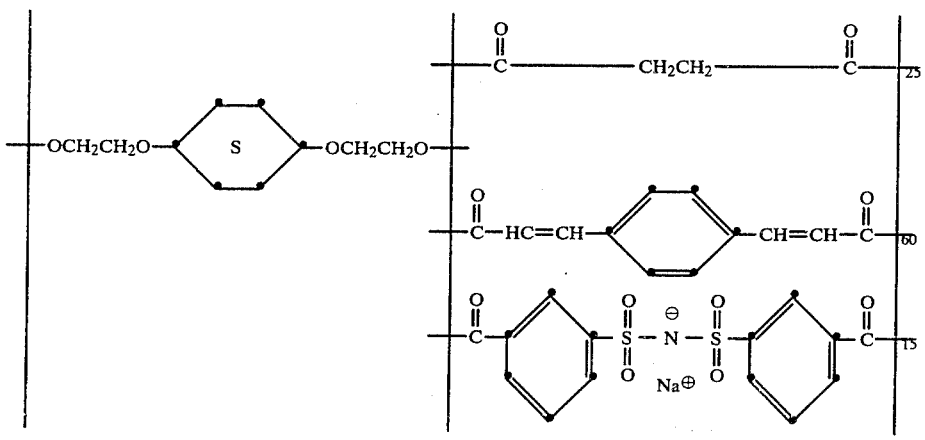

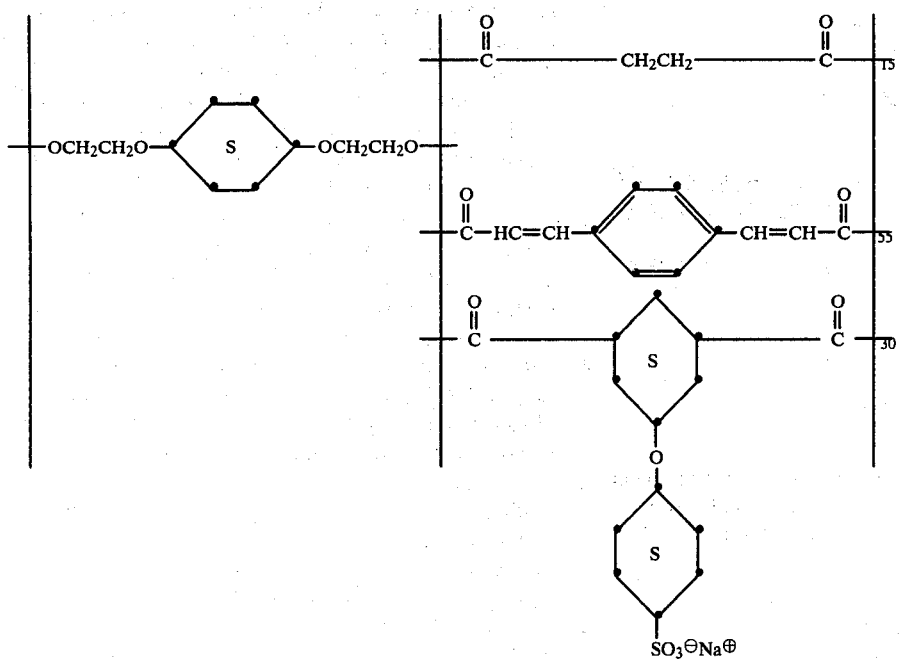

The optimum concentration of photosensitive polyesterionomer in the photopolymer layer will vary depending upon such factors as the dye to be imbibed, the particular mordant in the mordant layer, the desired image and processing conditions. A useful concentration of polyesterionomer in the photopolymer layer is within the range of about 0.01 mg to about 20 mg of polyesterionomer per square decimeter, and preferably about 2.0 mg to about 10 mg of polyesterionomer per square decimeter.

Many mordants are useful in the mordant layer according to the invention. The mordant must be one that does not adversely affect the photohardening capability of the polyesterionomer, including solution properties necessary for coating and adhesion properties. The mordant must also be one which is capable of being retained on the support throughout exposure, development and dye imbibition steps in processing according to the invention.

Useful mordants, preferably polymeric mordants, include many mordants which are useful in various photographic films and papers, and which contain repeating monomeric units containing charge-bearing cationic groups.

A useful mordant is, for example, a polymer having a repeating unit represented by the formula:

wherein:

T is an organo group and is a portion of a polymer backbone, including such organo groups as 1,2,2-ethylidyne, 1-carboxy-1,2,2-ethylidyne, 1,3,4-succinimidetriyl, 1-carbamoyl-1,2,2-ethylidyne and 2-methyl-1,2,2-ethylidyne;

Q is a chemical bond or chemical group linking $Z^{\oplus}$ to T, such as arylenealkylene, for example, phenylenemethylene, arylene, alkylene or amido, an arylene ester or amide, such as carbamoyloxyethyl, carbonyliminophenyl, carbonyliminoethyl and carbonyloxyphenyl;

$X^{\ominus}$ is an acid anion, such as chloride, bromide, nitrate, methosulfate and p-toluenesulfonate; and, $Z^{\oplus}$ is a cationic group, preferably a quaternary ammonium or phosphonium group.

Preferably, Q represents a hydrocarbon group containing 5 to 20 carbon atoms, such as arylene including phenylene and naphthylene, arylenealkylene, such as phenylenemethylene and phenyleneethylene, arylenebisalkylene, such as phenylenedimethylene and phenylenediethylene, alkylenebisarylene, such as isopropylidenediphenylene and methylenediphenylene, as well as alkylene, alkylenearylene and other groups listed above additionally linked to -T- through an ester, amide or ether group, or containing other amide (—CONH—) or ester (—COO—) linking groups, such as carbonyloxyethyl, carbonyliminomethylenephenylenemethylene, carbonyloxyethyleneoxycarbonylphenylene and carbonyloxypropylene.

In especially useful embodiments of the invention, $Z^{\oplus}$ represents a quaternary ammonium group represented by the formula:

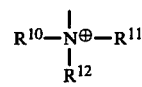

wherein each one of $R^{10}$, $R^{11}$ and $R^{12}$, which are the same or different, is aryl, aralkyl or alkaryl containing 6 to 20 carbon atoms or alkyl containing 1 to 10 carbon atoms. Examples of useful groups include phenyl, naphthyl, phenylethyl, benzyl, isopropylphenyl, methyl, ethyl, cyclohexyl and decyl.

Another example of a useful mordant is one having the repeating unit represented by the formula:

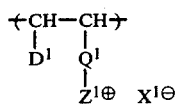

wherein:

$D^1$ is hydrogen or a chemical group linked with $Q^1$;
$Q^1$ is a chemical bond(s) or a chemical group linking $Z^{1\oplus}$ to the vinyl carbon atom,
$Z^{1\oplus}$ represents a heterocyclic ring of the structure:

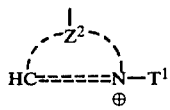

wherein $T^1$ is hydrogen, aralkyl containing 7 to 20 carbon atoms, such as benzyl, phenethyl and naphthylethyl, or alkyl containing 1 to 5 carbon atoms; such as

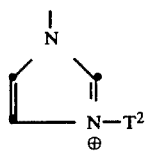

wherein $Z^2$ is the number of non-metallic atoms, especially carbon, nitrogen and oxygen atoms, necessary to complete a saturated or unsaturated ring; and $T^2$ is the same as $T^1$; and, $X^{1-}$ is an acid anion, such as chloride, bromide, nitrate, methosulfate and p-toluenesulfonate.

Alkyl in the above groups includes alkyl substituted with groups that do not adversely affect the desired mordanting properties of the mordant. An example of a substituted alkyl group is 2-hydroxyethyl. Within the mordant formulas, a protonated polyvinylimidazole mordant is especially useful.

A particularly useful mordant is one having the repeating unit represented by the formula:

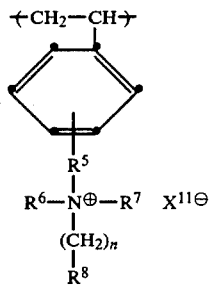

wherein:

$R^5$ is alkylene containing 1 to 4 carbon atoms, such as methylene, ethylene and butylene;
$R^6$ and $R^7$ are the same or different and each is aryl, aralkyl or alkaryl containing 6 to 20 carbon atoms, or alkyl containing 1 to 10 carbon atoms;
n is 0, 1 or 2;
$R^8$ is methyl or phenyl;
$X^{11\ominus}$ is an acid anion, such as chloride, bromide, nitrate, methosulfate, and p-toluenesulfonate.

The polymeric mordants in the mordant layer in an element according to the invention are homopolymers or copolymers. An illustrative listing of representative mordants includes recurring units as described and up to 75 weight percent of added recurring units comprising the residue of noninterfering monomers. The term "noninterfering monomers" means herein chemical units which do not chemically or physically interfere with mordanting of anionic dyes according to the invention. Monomers which provide such noninterfering repeating units include olefinic, aliphatic and aromatic hydrocarbons, such as olefins, substituted olefins, such as styrene and substituted styrene, alkyl acrylates and methacrylates and derivatives of these monomers. If desired, polymeric mordants useful in a mordant layer of an element according to the invention are crosslinked to provide individual polymeric chains which are, for example, covalently crosslinked by difunctional crosslinking groups, such as divinylbenzene and ethylene dimethacrylate. When such difunctional crosslinking groups are present, they constitute about 0.1 to about 10 weight percent, preferably about 0.1 to about 2 weight percent, based on the total weight of monomers present in the copolymerizable blend of monomers useful for preparing such crosslinked polymers. Representative copolymers useful in a mordant layer of an element according to the invention are copolymerized by procedures known in the polymer art from a monomer blend containing (a) about 25 to about 99 weight percent of monomers based on one of the described mordant formulas; (b) about 1 to about 75 weight percent of monomers providing noninterfering repeating units; and, (c) 0 to 10 weight percent of a difunctional crosslinking agent.

While polymeric mordants are especially useful, long chain nonpolymeric compounds having the requisite cationic group to mordant anionic dyes are also useful, such as cetyltrimethylammonium bromide and 4-octadecyl-N-methylpyridinium chloride.

An illustrative listing of representative mordants useful in a mordant layer of an element according to the invention is as follows, the ratios stated being molar ratios:

TABLE I

| Mordant Number | Name and Structure |
|---|---|
| M1 | Poly[styrene-co-N—(3-maleimidopropyl)-N,N—dimethyl-N—benzylammonium chloride] (1:1) (also known as Poly(styrene-co-3-maleimidopropyl-N,N—dimethyl-N—benzyl ammonium chloride) (1:1) |
| | ![structure] |
| M2 | Poly(N—vinylbenzyl-N,N—dimethyl-N—allyl-ammonium chloride) |

TABLE I-continued

| Mordant Number | Name and Structure |
|---|---|
| | 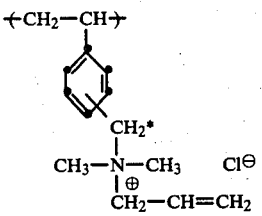 |

*The carbon bond to the phenyl ring is nonspecific as shown, because the monomeric mix can comprise both the meta and the para bonding positions; for example, it can be a mix comprising 55 percent by weight in the meta position and 45 percent by weight in the para position.

M3  Polyvinylimidazole**

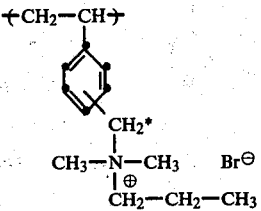

**This becomes cationic when one of the nitrogens of the imidazole group is protonated in an acid bath.

M4  Poly(N—vinylbenzyl-N,N—dimethyl-N—propargyl-ammonium bromide)

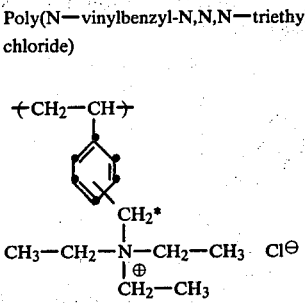

M5  Poly(styrene-co-N—vinylbenzyl-N,N—dimethyl-N—allylammonium chloride) (1:1)

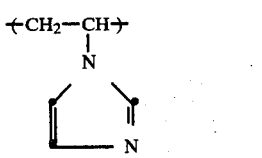

M6  Poly(vinyl pyridinium acetate chloride) (also known as Poly(N—vinyloxycarbonylmethyl-pyridinium chloride)

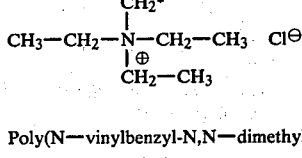

M7  Poly(N—vinylbenzyl-N,N—dimethyl-N—propyl-ammonium bromide)

TABLE I-continued

| Mordant Number | Name and Structure |
|---|---|
| | 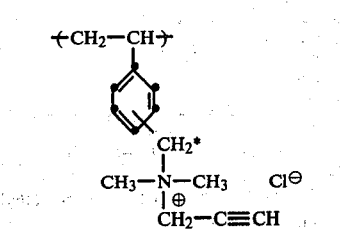 |

M8  Poly(N—vinylbenzyl-N,N,N—triethylammonium chloride)

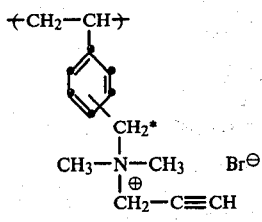

M9  Poly(N—vinylbenzyl-N,N—dimethyl-N—propargyl-ammonium chloride)

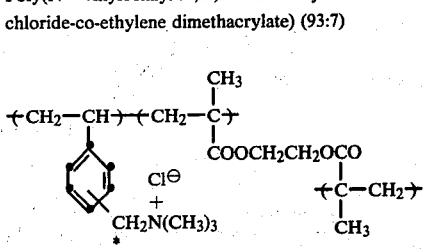

M10  Poly(N—vinylbenzyl-N,N,N—trimethylammonium chloride-co-ethylene dimethacrylate) (93:7)

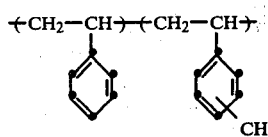

M11  Poly(N—vinylbenzyl-N,N—dimethyl-N—allyl-ammonium bromide-co-divinylbenzene) (95:5)

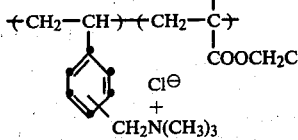

M12  Poly(styrene-co-N—vinylbenzyl-N,N—dimethyl-N—allylammonium bromide-co-divinylbenzene) (49:49:2)

TABLE I-continued

| Mordant Number | Name and Structure |
|---|---|
| | ![structure: poly with three CH2-CH units, phenyl rings, one bearing CH2N⁺(CH3)(CH3)CH2-CH=CH2 Br⁻] |
| M13 | Poly(N—vinylbenzyl-N,N—dimethyl-N—2-butenyl-ammonium chloride) |
| | ![structure: CH2-CH with phenyl, CH2-N⁺(CH3)(CH3)-CH2-CH=CH-CH3, Cl⁻] |
| M14 | Poly(styrene-co-N—vinylbenzyl-N,N—dimethyl-N—allylammonium chloride) (1:4) |
| | ![structure: styrene-co-vinylbenzyl CH2-N⁺(CH3)(CH3)-CH2-CH=CH2, Cl⁻] |
| M15 | Poly(styrene-co-N—vinylbenzyl-N,N,N—trimethylammonium chloride) (1:1) |
| | ![structure: styrene-co-vinylbenzyl CH2-N⁺(CH3)(CH3)(CH3), Cl⁻] |
| M16 | Poly[styrene-co-N—(3-acrylamidopropyl)-N—benzyl-N,N—dimethylammonium chloride] (1:1) |
| M17 | Poly(N—vinylbenzyl-N—benzyl-N,N—dimethyl-ammonium chloride) |
| M18 | Poly(styrene-co-N—vinylbenzyl-N,N—dimethyl-N—butylammonium chloride) (1:1) |
| | ![structure: styrene-co-vinylbenzyl CH2-N⁺(CH3)(CH3)-CH2-CH2-CH2-CH3, Cl⁻] |
| M19 | Poly(1-vinylimidazole-co-1-vinyl-3-benzylimidazolium chloride) (1:1) |
| M20 | Poly(1,2-dimethyl-5-vinylpyridinium p-toluenesulfonate) |
| M21 | Poly(1-benzyl-4-vinylpyridinium chloride) |
| M22 | Poly[1-benzyl-2-methyl-5-vinylpyridinium chloride] |
| M23 | Poly(N—vinylbenzyl-N,N—dimethyl-N—carbamoyl-methylammonium chloride) |
| | ![structure: CH2-CH phenyl, CH2-N⁺(CH3)(CH3)-CH2C(O)-NH2, Cl⁻] |
| M24 | Poly(N—vinylbenzyl-N,N—dimethyl-N—cyclohexyl-ammonium chloride) |
| | ![structure: CH2-CH phenyl, CH2-N⁺(CH3)(CH3)-thiane ring, Cl⁻] |
| M25 | Poly[N—vinylbenzyl-N,N—dimethyl-N—(3-methyl-2-butenyl)ammonium chloride] |
| | ![structure: CH2-CH phenyl, CH2-N⁺(CH3)(CH3)-CH2-CH=C(CH3)(CH3), Cl⁻] |
| M26 | Poly(styrene-co-N—vinylbenzyl-N,N,N—trimethyl-ammonium chloride) (1:2) |
| | ![structure: styrene-co-vinylbenzyl CH2-N⁺(CH3)(CH3)(CH3), Cl⁻] |
| M27 | Poly(N—vinylbenzyl-N,N—dimethyl-N—isobutyl-ammonium chloride) |
| | ![structure: CH2-CH phenyl, CH2-N⁺(CH3)(CH3)-CH2-CH(CH3)(CH3), Cl⁻] |
| M28 | Poly[N—(2-acrylamido-2-methylbutyl)-N,N—dimethyl-N—benzylammonium chloride] |
| M29 | Poly(N,N,N—trimethyl-N—vinylbenzylammonium chloride) |

TABLE I-continued

| Mordant Number | Name and Structure |
|---|---|
| | ![structure: poly(vinylbenzyl trimethylammonium chloride)] +CH2—CH+ with phenyl, CH2—N⊕(CH3)3 Cl⊖ |
| M30 | Poly(styrene-co-N—vinylbenzyl-N—benzyl-N,N—dimethylammonium chloride) (also known as Poly(styrene-co-benzyl(dimethyl)-p-vinyl-benzylammonium chloride)) |
| M31 | Poly(P,P,P—trioctyl-P—vinylbenzylphosphonium chloride) |
| M32 | Poly(styrene-co-N—vinylbenzyl-N,N,N—trihexyl-ammonium chloride) |
| | +CH2—CH+ +CH2—CH+ styrene/vinylbenzyl-N⊕(C6H13)3 Cl⊖ |
| M33 | Poly(styrene-co-N,N,N—trimethyl-ammonium chloride) (also known as Poly(N,N,N—trimethylvinylbenzylammonium chloride-co-styrene) |
| | +CH2—CH+ +CH2—CH+ styrene/vinylbenzyl-CH2—N⊕(CH3)3 Cl⊖ |
| M34 | Poly(styrene-co-N—vinylbenzyl-N,N—dimethyl-N—benzylammonium chloride-co-divinylbenzene) (49:49:2) |
| M35 | Poly(N—vinylbenzylpiperidinium chloride) |
| | +CH2—CH+ phenyl-CH2—NH⊕-piperidine Cl⊖ |
| M36 | Poly{N—[N'—(4-vinylphenylcarbamoyl)methyl]-N,N,N—trimethylammonium chloride} (also known as Poly(4-vinylphenylcarbamylmethyl-N,N,N—trimethylammonium chloride)) |
| M37 | Poly(N—vinylbenzyl-N,N—dimethyl-N—acetonyl-ammonium chloride) |
| | +CH2—CH+ phenyl-CH2—N⊕(CH3)2—CH2—C(=O)—CH3 Cl⊖ |
| M38 | Poly(N—vinylbenzyl-N,N—dimethyl-N—methoxycarbonylmethylammonium chloride) |
| | +CH2—CH+ phenyl-CH2—N⊕(CH3)2—CH2—C(=O)—O—CH3 Cl⊖ |
| M39 | Poly(1-vinylbenzylpyridinium chloride) (also known as Poly(vinylbenzyl-1-pyridinium chloride)) |
| | —CH2—CH+ phenyl-CH2—N⊕(pyridinium) Cl⊖ |
| M40 | Poly(1-vinylbenzyl-1-methylpyrrolidinium chloride) (also known as Poly(vinylbenzyl-N—methyl-1-pyrrolidinium chloride)) |
| | +CH2—CH+ phenyl-CH2—N⊕(CH3)(pyrrolidinium) Cl⊖ |
| M41 | Poly(1-vinylbenzyl-1-methylpiperidinium chloride) (also known as Poly(vinylbenzyl-N—methyl-1-piperidinium chloride)) |
| | +CH2—CH+ phenyl-CH2—N⊕(CH3)(piperidinium) Cl⊖ |
| M42 | Poly(vinylbenzyl-N—methyl-1-morpholinium chloride) |

TABLE I-continued

| Mordant Number | Name and Structure |
|---|---|
| M43 | Poly(N—vinylbenzyl-N,N—dimethylanilinium chloride) 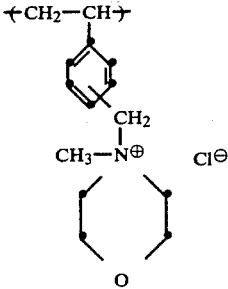 |
| M44 | Poly(styrene-co-N—vinylbenzyl-N,N—dimethyl-N—cyclohexylammonium chloride-co-divinylbenzene) (49:49:2) (also known as Terpoly[styrene:(vinylbenzyl)(dimethyl)(cyclohexyl) ammonium chloride-co-divinylbenzene] (49:49:2)) 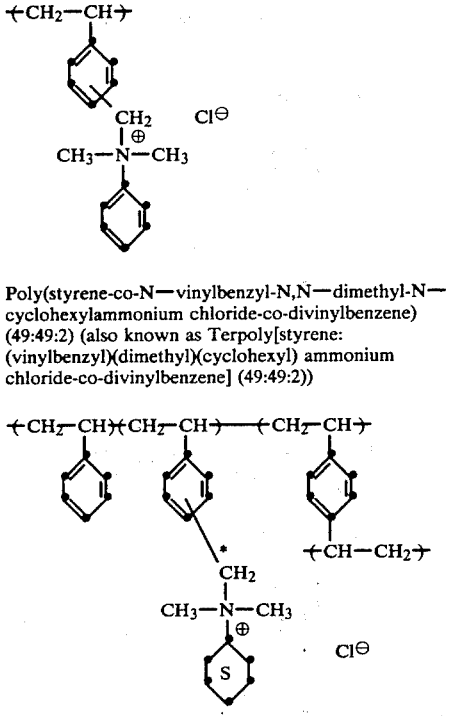 |

The mark * for the mordants listed indicates that the carbon bond to the phenyl ring is nonspecific because the monomeric mix comprises both the meta and the para bonding positions.

The mordants useful in a mordant layer of an element according to the invention are prepared by procedures known in the chemical synthesis art. Details of the preparation of useful mordants are described in the following patents: British Pat. No. 1,261,925; and U.S. Pat. Nos. 3,488,706; 3,557,066; 3,625,694; 3,709,690; 3,770,439; 3,758,445; 3,773,509; 3,859,096; 3,898,088; 3,944,424 and 3,958,995.

The optimum useful concentration of mordant in a mordant layer of an element according to the invention will depend upon such factors as molecular weight and mordanting strength of the mordant, desired image, processing conditions and particular photopolymer in the photohardenable layer contiguous to the mordant layer. A useful concentration of mordant in the mordant layer is within the range of 1.0 to 30 mg of mordant per square decimeter of support, preferably within the range of 2 to 16 mg of mordant per square decimeter of support.

For color proofing use, a preferred range of photopolymer is within the range of 1.0 to 25 mg of photopolymer per square decimeter of support, and a preferred range of mordant is within the range of 2 to 16.0 mg of mordant per square decimeter of support.

The photopolymer and mordant layers are generally not self supporting. The mordant layer is generally on a support, with the photopolymer layer being on the mordant layer. A conventional support that is useful in the photographic art is also useful as a support for an element according to the invention. Useful supports include transparent supports, such as transparent film and glass supports. Supports that are either opaque or translucent are also useful, such as photographic paper supports and metal supports. A transparent poly(ethylene terephthalate) film support is especially useful. Useful supports are described in, for example, Research Disclosure, December 1978, page 28, Item No. 17643, published by Industrial Opportunities, Limited, Homewell, Havant, Hampshire, PO91EF, United Kingdom. The support generally contains one or more subbing layers to alter the support's surface properties to enhance adhesion of the mordant layer to the support.

The layers of an element according to the invention are generally coated from an aqueous composition onto the support or layer. Examples of useful coating procedures are described in the above Research Disclosure publication. Coating aides are often useful in the coating composition.

An overcoat layer which does not adversely affect exposure, processing and dye imbibition according to the invention is useful on the photopolymer layer of an element according to the invention. An example of a useful overcoat layer is a poly(vinyl pyrrolidone) overcoat layer.

The cationic mordant layer of an element according to the invention is preferably contiguous to the photosensitive polyesterionomer layer. It is generally disadvantageous to have an interlayer between the cationic mordant layer and the photosensitive polyesterionomer layer because the continuous tone dye image produced in the element is generally adversely affected by the interlayer. If at least one interlayer is present between the cationic mordant layer and the photosensitive polyesterionomer layer, a material comprising the interlayer must be selected which does not adversely affect the photosensitive and other desired properties of the photosensitive polyesterionomer and does not adversely affect the desired mordanting properties of the mordant layer. An optimum interlayer will depend upon such factors as the particular mordant, the particular photosensitive polyesterionomer, the dye to be imbibed, desired image and processing conditions. Such an interlayer comprises, for example, gelatin, poly(vinyl alcohol) or poly(vinylpyrrolidone).

The word "superposed" herein means that the cationic mordant layer and the photosensitive polyesterionomer layer of a dye imbibition imaging element according to the invention are in a location in the element which enables the desired dye imbibition to take place. The word "superposed" includes the preferred location of the cationic mordant layer and the photosensitive polyesterionomer contiguous to each other. "Superposed" alternatively includes a location of at least one interlayer between the cationic mordant layer and the photosensitive polyesterionomer layer.

An example of a useful dye imbibition imaging element for producing a positive, continuous tone, dye image comprises a support having thereon:
(a) a cationic mordant layer consisting essentially of poly(styrene-co-N-vinylbenzyl-N,N-dimethyl-N-cyclohexylammonium chloride-co-divinylbenzene) (49:49:2), having superposed thereon, preferably contiguous thereto:
(b) a sensitized photohardenable photopolymer layer consisting essentially of poly[1,4-cyclohexylenebis-(oxyethylene) succinate-co-p-phenylenebis(acrylate)-co-5-sodiosulfoisophthalate].

Another example of a dye imbibition imaging element for producing a positive, continuous tone, dye image comprises a support having thereon:
(a) a cationic mordant layer consisting essentially of poly(styrene-co-N-vinylbenzyl-N,N-dimethyl-N-cyclohexylammonium chloride-co-divinylbenzene) (49:49:2) having superposed thereon, preferably contiguous thereto:
(b) a sensitized photohardenable photopolymer layer consisting essentially of poly[1,4-cyclohexylenebis-(oxyethylene) succinate-co-p-phenylenebis(acrylate)-co-5-(4-sodiosulfophenoxy)isophthalate].

A further example of a dye imbibition imaging element for producing a positive, continuous tone, dye image comprises a support having thereon:
(a) a cationic mordant layer consisting essentially of poly(styrene-co-N-vinylbenzyl-N,N-dimethyl-N-cyclohexylammonium chloride-co-divinylbenzene) (49:49:2) having superposed thereon, preferably contiguous thereto:
(b) a sensitized photohardenable photopolymer layer consisting essentially of poly[1,4-cyclohexylenebis-(oxyethylene) succinate-co-phenylenebis(acrylate)-co-3,3'-sodioiminodisulfonyldibenzoate].

Another especially useful example of a dye imbibition imaging element for producing a positive, continuous tone, dye image comprises a support having thereon:
(a) a cationic mordant layer consisting essentially of poly(styrene-co-N-vinylbenzyl-N,N-dimethyl-N-cyclohexylammonium chloride-co-divinylbenzene) (49:49:2) having superposed thereon, preferably contiguous thereto:
(b) a sensitized photohardenable photopolymer layer consisting essentially of poly[1,4-cyclohexylenebis-(oxyethylene)succinate-co-p-phenylenebis(acrylate)-co-5-(4-sodiosulfocyclohexyloxy)-1,3-cyclohexanedicarboxylate].

A process for forming a positive, continuous tone, dye image in a dye imbibition imaging element according to the invention comprises the steps of:
(i) imagewise exposing said photopolymer layer to activating radiation to imagewise harden the photopolymer layer;
(ii) developing said photopolymer layer by water rinsing; and, then
(iii) imbibing an anionic dye into said mordant layer through the unexposed areas of said photopolymer layer.

The activating radiation for exposure of the photopolymer layer is generally primarily ultraviolet (UV) radiation. Other radiation sources to which the sensitized photopolymer in the photopolymer layer is sensitive are useful, such as lasers and conventional light sources. The time and intensity of imagewise exposure should be sufficient to imagewise harden the photopolymer to a desired degree to enable subsequent development. For preparation of color-proofing overlays, conventional contact exposure techniques found useful in photography are also useful for imagewise exposure of the element according to the invention.

Following imagewise exposure, development of the element is achieved generally by merely water rinsing the element. The term "water" herein means distilled water and conventional drinking water. The term also includes aqueous solutions containing components, such as metal ions, which do not adversely affect the photopolymer layer and mordant layer of the element according to the invention. Alternatively, development is achieved by a mixture of water and a suitable organic solvent, such as ethanol. A minor concentration of an alkali, such as sodium hydroxide, is also useful in the water, if desired. Aqueous solutions which contain compounds which hinder photohardening to an undesired degree or which are anionic to a sufficient degree to hinder satisfactory subsequent dye imbibition are to be avoided.

The terms "developing" and "development" herein mean the removal of at least part of the unhardened image areas in the photopolymer layer according to the invention after imagewise exposure. This is accomplished generally by said step of water rinsing the element.

Optimum development conditions, such as time, temperature and pressure, will vary, depending upon such factors as the desired image, particular photopolymer and mordant, and particular dyes to be imbibed after development. The development step is generally carried out at about room temperature (about 21° C.) at about atmospheric pressure. The time of development will depend upon the described factors and upon the means for developing. A useful rinse time is generally within the range of about 2 seconds to about 1 minute.

The term "rinsing" herein includes washing, spraying, immersing and otherwise passing water onto or contacting the exposed element with water to a sufficient degree to cause unexposed portions of the photopolymer layer to be removed to facilitate subsequent imbibing of the anionic dye into the mordant layer in the unexposed areas of the element. Removing unexposed portions of the photopolymer also allows more rapid transfer of dye from the unexposed areas of the element to a mordant containing a receiver layer, if desired. Alternatively, the rinsing is achieved by light mechanical rubbing or buffing by means of a material soaked in water. The portions of photopolymer remaining on the element after rinsing will be in proportion to the amount of light that has struck the photopolymer layer. The rinsing does not remove the mordant layer. The rinsing is generally carried out by means of a soft spray of ordinary tap water or simply a stream of water from an ordinary faucet.

After development of the element, at least one anionic dye is imbibed into the mordant layer of the element. Alternatively, at least one anionic dye is imbibed into the mordant layer of the element through the unexposed portions of the photopolymer layer without the need of removing part of the photopolymer layer. In both processes, the anionic dye is at least temporarily immobilized in the mordant layer. Imbibing of the anionic dye is generally accomplished by immersing the element in a suitable anionic dye bath. A preferred anionic dye bath is a water solution or an aqueous buffer solution of an anionic dye, as described hereinafter in more detail. The optimum conditions for imbibing at least one anionic dye into the element will vary, depending upon such factors as the desired image, particular mordant, particular photopolymer, particular anionic dye and solvent for the anionic dye bath. A useful time for immersing an element into a dye bath is within the range of about 10 seconds to about 150 seconds, preferably about 25 seconds to about 75 seconds. A useful temperature of the anionic dye bath is within the range of about 10° C. to about 40° C., preferably within the range of about 15° C. to about 30° C. After the desired amount of dye is imbibed into the element, the element is removed from the bath. The element is then optionally rinsed to remove excess anionic dye. Each of the processing steps is generally carried out within the same temperature range, such as at a temperature within the range of about 10° C. to about 40° C. Following processing, the element is dried by a heating means, such as by means of a heated air blower. Optionally, the element is dried without use of a heating means.

Many anionic dyes are useful to form an image in the element according to the invention. The optimum dye selected will depend upon such factors as the desired image, processing conditions and particular mordant. For instance, for color separation in forming a composite color-proofing overlay, anionic dyes are selected that provide subtractive color, that is, cyan, magenta and yellow dyes. Anionic black dyes are also useful. Examples of useful magenta dyes are represented by the formula:

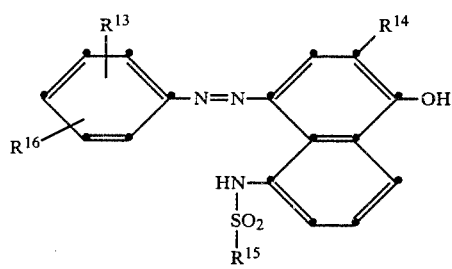

wherein:
$R^{13}$ is an electron withdrawing group, such as $-SO_2CH_2CH_2COOH$, sulfamoyl, carboxyl, $-SO_3H$, $-SO_2CH_3$, alkyl containing 1 to 3 carbon atoms,

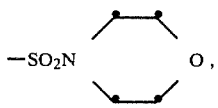

$-SO_2CH(CH_3)_2$, $-SO_2CF_3$;

$R^{14}$ is an electron withdrawing group, such as $-SO_2CH_2CH_2COOH$, $-SO_2NHCH_2COOH$, halogen, $-SO_2NHC(CH_3)_3$, $-SO_2NHCH_3$, $-SO_2N(C_2H_5)_2$, $-SO_2N(CH_3)_2$,

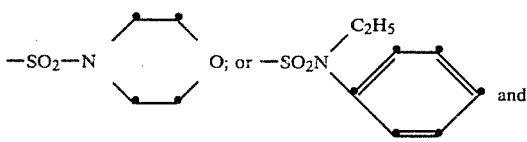

$R^{15}$ is an electron withdrawing group, such as alkyl containing 1 to 3 carbon atoms, including methyl, ethyl and propyl;

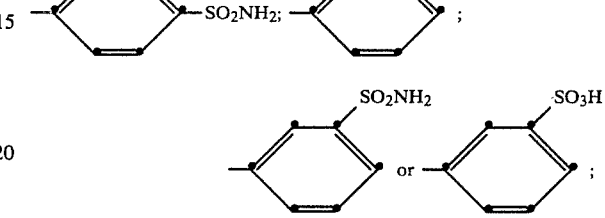

and
$R^{16}$ is nitro, hydrogen or halogen, including chlorine, bromine, iodine or fluorine.

Acid Fuchsin, Color Index 1740, is an example of another useful magenta dye.

Examples of useful yellow dyes are represented by the formula:

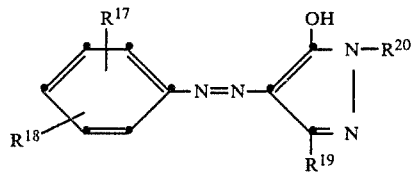

wherein:
$R^{17}$ is $-SO_2NHCH_2COOH$, $-SO_3H$, $-SO_2NH_2$, halogen, carboxyl or $-CONHCH_2COOH$;
$R^{18}$ is alkoxy containing 1 to 3 carbon atoms, hydrogen, halogen or carboxyl;
$R^{19}$ is hydrogen, hydroxy, alkyl containing 1 to 3 carbon atoms, such as methyl, ethyl and isopropyl, cyano, carboxyl, carbonamido or carbamoyl; and,
$R^{20}$ is:

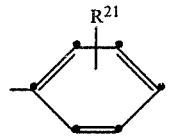

wherein $R^{21}$ is $-SO_3H$, $-COOH$, chlorine or hydrogen. Other examples of useful yellow dyes are represented by the formula:

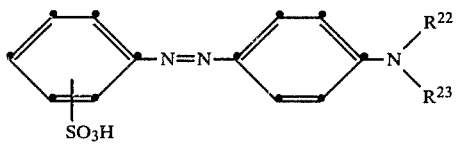

wherein:

$R^{22}$ is alkyl containing 1 to 3 carbon atoms; and $R^{23}$ is —$C_2H_4SO_3H$, alkyl containing 1 to 3 carbon atoms, or —$C_2H_4NHSO_2CH_3$.

Examples of useful black dyes include water-soluble azo black dyes, preferably bisazo black dyes, which provide the desired degree of imbibition into an element according to the invention. One illustrating class of useful black dyes is represented by the formula:

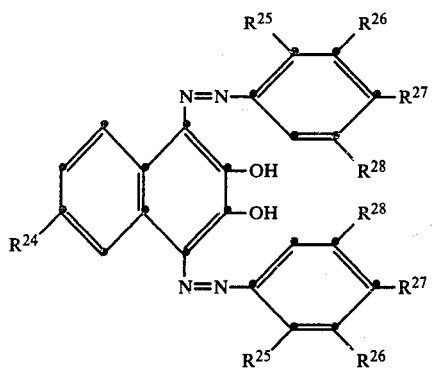

wherein:

$R^{24}$ and $R^{28}$ are individually hydrogen; —$SO_3Na$; —$SO_3H.NH_3$; —$SO_3H.$pyridine; —$SO_3H.H_2NCH_2C$-$H_2OH$; —$SO_3H.N(C_2H_5)_3$; —$SO_2NH_2$; —COOH or —$CH_2OH$;

$R^{25}$ and $R^{27}$ are individually hydrogen; —OH; —$OCH_3$; —$OCH_2COOCH_2CH_3$ or —$OCH_2COOH$; and, $R^{26}$ is hydrogen; —COOH; —$CH_2OH$ or —$CONHCH_2COOH$;

wherein $R^{24}$, $R^{25}$, $R^{26}$, $R^{27}$ and $R^{28}$ together provide water solubility of at least 0.5 grams of the black dye per liter of water at 21° C.

The water soluble black dyes are prepared by methods known in the organic compound synthesis art. Illustrative black dyes are described in, for example, copending U.S. Ser. No. 185,853 of H. G. McGuckin, L. J. Rossi and A. L. Johnson, filed Sept. 10, 1980.

The following Table II is an illustrative list of representative examples of useful dyes:

TABLE II

| Dye No. | Structure | Color |
|---|---|---|
| D1 | 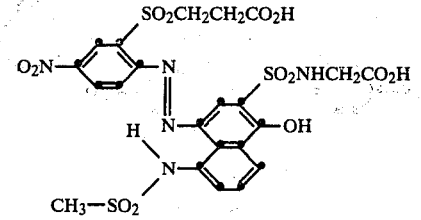 | Cyan |
| D2 | 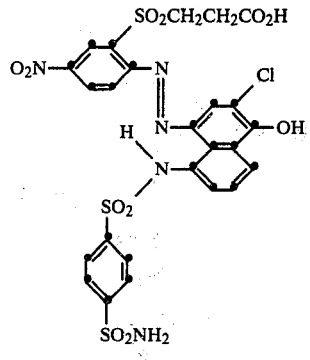 | Cyan |
| D3 | 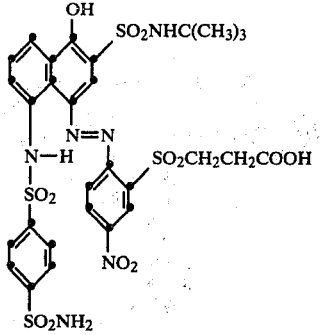 | Cyan |

TABLE II-continued

| Dye No. | Structure | Color |
|---|---|---|
| D4 | (chemical structure) | Cyan |
| D5 | (chemical structure) | Cyan |
| D6 | (chemical structure) | Cyan |
| D7 | (chemical structure) | Cyan |
| D8 | (chemical structure) | Cyan |

TABLE II-continued

| Dye No. | Dyes Structure | Color |
|---|---|---|
| D9 | 2-nitro-6-(2-carboxyethylsulfonyl)phenylazo-1-hydroxy-2-(N,N-dimethylsulfamoyl)-8-(methylsulfonylamino)naphthalene | Cyan |
| D10 | 4-sulfamoylphenylazo-1-hydroxy-2-(N-carboxymethylsulfamoyl)-8-(methylsulfonylamino)naphthalene | Magenta |
| D11 | 2-carboxyphenylazo-1-hydroxy-2-(N-tert-butylsulfamoyl)-8-(methylsulfonylamino)naphthalene | Magenta |
| D12 | 4-sulfophenylazo-1-hydroxy-2-(N-carboxymethylsulfamoyl)-8-(methylsulfonylamino)naphthalene | Magenta |
| D13 | 3-sulfamoylphenylazo-1-hydroxy-2-(N-carboxymethylsulfamoyl)-8-(methylsulfonylamino)naphthalene | Magenta |
| D14 | 2-(methylsulfonyl)phenylazo-1-hydroxy-2-(N-carboxymethylsulfamoyl)-8-(methylsulfonylamino)naphthalene | Magenta |
| D15 | 2-chloro-5-sulfophenylazo-1-hydroxy-2-(N-carboxymethylsulfamoyl)-8-(methylsulfonylamino)naphthalene | Magenta |

TABLE II-continued

| Dye No. | Dyes Structure | Color |
|---|---|---|
| D16 | [structure: 4-chloro-3-sulfophenyl azo naphthalene with OH, SO₂NHCH₂COOH, and HNSO₂CH₃ substituents] | Magenta |
| D17 | [structure: indanedione-based dye with OH, CO₂H, and NH groups] | Yellow |
| D18 | [structure: 4-sulfophenylazo-pyrazolone with OH, CH₃, N-phenyl] | Yellow |
| D19 | [structure: 3-carboxy-4-sulfamoylphenylazo pyrazole with OH, CN, N-phenyl] | Yellow |
| D20 | [structure: sulfamoylmethylcarboxy phenylazo pyrazole with HO, CN, N-phenyl] | Yellow |
| D21 | [structure: 3-sulfophenylazo-4-(N-ethyl-N-ethylsulfonate)aniline] | Yellow |
| D22 | [structure: 3-sulfophenylazo-4-dimethylaminobenzene] | Yellow |
| D23 | [structure: 4-sulfophenylazo-pyrazole with OH, N-phenyl] | Yellow |
| D24 | [structure: 4-sulfophenylazo-pyrazole with OH, OH, N-phenyl] | Yellow |
| D25 | [structure: 4-sulfamoylphenylazo-pyrazole-N-(3-sulfophenyl) with OH] | Yellow |
| D26 | [structure: 4-sulfophenylazo-pyrazole with OH, CONH₂, N-phenyl] | Yellow |

TABLE II-continued

| Dye No. | Structure | Color |
|---|---|---|
| D27 | 3-(sulfophenyl)azo-4-(N-ethyl-N-(2-(methylsulfonylamino)ethyl)amino)benzene | Yellow |
| D28 | 1-(4-carboxyphenyl)-4-((3-chlorophenyl)azo)-5-hydroxy-3-methylpyrazole | Yellow |
| D29 | 1-(4-carboxyphenyl)-4-((2-carboxyphenyl)azo)-5-hydroxy-3-methylpyrazole | Yellow |
| D30 | bis-pyrazolone methine (HO$_3$S-aryl, CH$_3$) | Yellow |
| D31 | 1-(4-sulfophenyl)-3-carboxy-4-((4-sulfophenyl)azo)-5-hydroxypyrazole | Yellow |
| D32 | 3-cyano-4-((sulfonamidoacetic acid phenyl)azo)-5-hydroxy-1-phenylpyrazole | Yellow |
| D33 | azo dye with SO$_2$CH$_2$CH$_2$COOH, OH, SO$_3$H, HNSO$_2$CH$_3$ substituents | Magenta |
| D34 | bis-azo naphthalene with CH$_3$O, OH, OH, SO$_3$H·pyridine, NaSO$_3$, CH$_3$O substituents | Black |

TABLE II-continued

| Dye No. | Dyes Structure | Color |
|---|---|---|
| D35 | 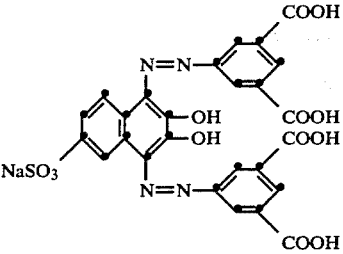 | black |
| D36 | 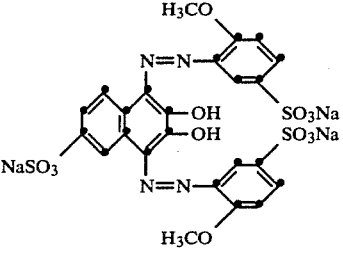 | black |
| D37 | 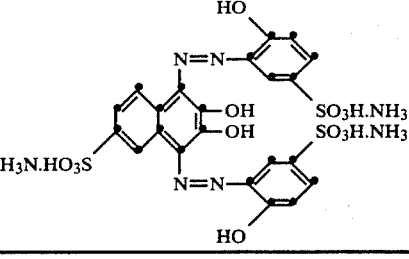 | black |

Other examples of useful dyes are described in *Research Disclosure*, May 1978, Item No. 16976, the disclosure of which is hereby incorporated by reference.

The described dyes are prepared by conventional synthesis techniques.

The optimum concentration of dye in the dye bath will depend upon the described factors, including the desired image, processing conditions, particular dye and particular mordant. A useful concentration is within the range of about 0.1 percent by weight to about 5.0 percent by weight of dye, preferably within the range of about 0.2 percent by weight to about 1.0 percent by weight of dye in the dye bath. The solvent in the anionic dye bath is water or water buffered to a pH suitable for the particular dye in the bath. For instance, a useful anionic dye bath contains a concentration of potassium phosphate and sodium hydroxide sufficient to produce a pH of about 10.0.

By suitable selection of dye colors, a color-separation element suitable for color-proofing is prepared. Should a correction be necessary of one or more of the original color negatives from which the proof is prepared, a corrected negative is prepared, and a new color-proofing element is prepared according to the invention. Based on the element and process of the invention, it is unnecessary for preparing printing plates, to set up presses and actually print reproductions until the correct color of the negatives has been verified.

Transfer Material and Process

Alternatively, the dye image imbibed into an element according to the invention is transferred from the element, which functions as a sender layer, to a receiver element. The receiver element comprises a support and a receiver layer on the support comprising a cationic mordant of a greater mordanting strength than the mordanting strength of the sender layer. Such relative mordant strengths are determined by conventional competing mordant tests known in the photographic art, such as tests described in U.S. Pat. No. 3,958,995. By transferring the dye images in proper registration to a single receiver element, a full-color proof is produced.

According to this embodiment, a process for formation of a continuous tone, dye image in a receiver layer comprising a first cationic mordant of a predetermined mordanting strength comprises the steps of:

(a) imagewise exposing a sender element according to the invention comprising:
  (i) a support having thereon:
  (ii) a mordant layer consisting essentially of a second cationic mordant for an anionic dye, the second cationic mordant having a lesser mordanting strength than the first cationic mordant, and having superposed thereon and adjacent to the mordant layer:
  (iii) a sensitized photohardenable, photopolymer layer according to the invention to imagewise harden the photopolymer layer;

(b) developing the photopolymer layer consisting essentially of a photosensitive polyesterionomer, preferably a photosensitive polyesterionomer A, as described, to imagewise harden said photopolymer layer;

(b) developing said photopolymer layer by means of water by rinsing the photopolymer layer to form hardened image areas in the photopolymer layer;

(c) imbibing at least one anionic dye into the second cationic mordant layer, said dye being temporarily immobilized in the portions of the second cationic mordant corresponding to unexposed portions of said photopolymer layer; and, (d) imagewise transferring said anionic dye to said receiver layer by contacting the receiver layer with the side of the sender element containing the second cationic mordant in the presence of an aqueous solution that aids transfer of the anionic dye into the first cationic mordant.

An alternative process as described according to the invention for forming a positive, continuous tone, dye image in a receiver layer avoids the need of a development step. This alternative process involves imbibing at least one anionic dye through the unexposed areas of the photopolymer layer into the second cationic mordant layer without the need of removing portions of the photopolymer layer.

The receiver layer comprises any of the polymeric mordants listed in Table I, provided the receiver layer has a greater mordanting strength than the mordant of the sender layer. In addition, the receiver layer optionally includes a binder, such as gelatin. Gelatin hardening agents, such as formaldehyde and bis(vinylsulfonylmethyl)ether are useful in the receiver layer. The optimum concentration of mordant and binder, such as gelatin, in the receiver layer will depend upon such factors as the particular dye to be transferred, the desired image and transfer conditions. A useful concentration of mordant in the image receiver layer is within the range of about 5.0 mg/dm$^2$ (about 50 mg/ft$^2$) to about 50 mg/dm$^2$ (about 500 mg/ft$^2$). A useful concentration of binder in the receiver layer is within the range of about 0 to about 60 mg/dm$^6$ (600 mg/ft$^2$). A preferred receiver layer comprises about 10 mg/dm$^2$ to about 30 mg/dm$^2$ of mordant and about 30 mg/dm$^2$ to about 50 mg/dm$^2$ of gelatin containing a suitable hardener, such as formaldehyde.

The receiver element preferably comprises a support. The support materials described for the sender layer are also useful for the receiver element.

The transfer of the dye is preferably accomplished in a salt solution or a mixture of alcohol and water. For this purpose, either or both of the sender layer and receiver layer are presoaked in such a solution for a time sufficient to provide the desired concentration of salt solution or mixture of alcohol and water in the layer. The time of soaking is generally within the range of about 10 to about 100 seconds. Thereafter, the two layers are contacted together, such as in a sandwich, and pressed, such as by means of rollers. The layers are permitted to remain in contact for a time sufficient to enable the desired concentration of dye to pass from the sender layer to the receiver layer, generally a time within the range of about 5 seconds to about 100 seconds. Thereafter, the two layers are separated.

Alternatively, the receiver layer is produced with the transfer salt incorporated in the receiver layer. A brief soak, such as up to about 5 seconds, of the sender layer is then useful.

Selection of an optimum salt solution for transfer of the dye depends primarily upon the solubility of the mordanted dye. Useful salt solutions comprise potassium chloride, bromide and iodide, sodium salicylate, and potassium thiocyanate. Concentrations of such salt solutions are within the range of about 0.1 molar to about 1.0 molar.

Alcohol and water solutions useful in the transfer process comprise mixtures wherein the concentration of alcohol is equal to or up to five times the concentration in volume of water. Methanol, ethanol and isopropanol are examples of useful alcohols.

It is useful, if desired, to redye the sender layer after transfer by immersing the original sender layer in the same dye bath.

Figure 1:
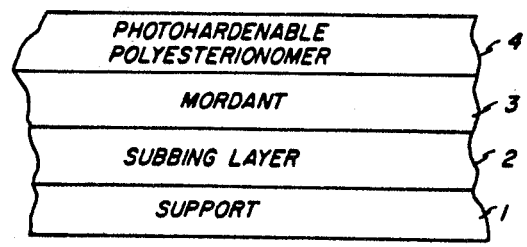
FIG. 1 illustrates schematically a dye imbibition imaging element according to one illustrative embodiment of the invention.

According to illustrative FIG. 1, an element according to the invention comprises a support 1 having thereon a subbing layer 2, a mordant layer 3 and a photohardenable polyesterionomer layer 4. The subbing layer 2 helps the mordant layer 3 to adhere to the support 1.

Figure 2:
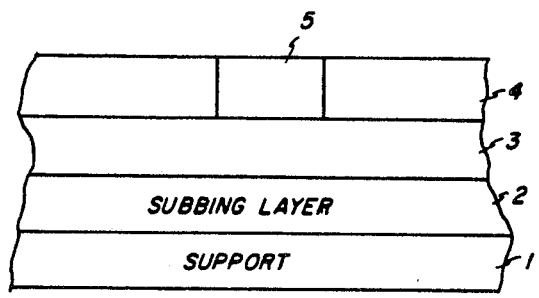
FIG. 2 illustrates schematically a dye imbibition imaging element after imagewise exposure to produce imagewise photohardening of the photohardenable layer.

Upon imagewise exposure of the element of FIG. 1, an element like that of FIG. 2 is formed having an area 5 which is not imagewise hardened in photohardenable polyesterionomer layer 4 because area 5 is an unexposed area of the element. Portions of layer 4 of FIG. 2 that are exposed to activating radiation are photohardened.

Figure 3:
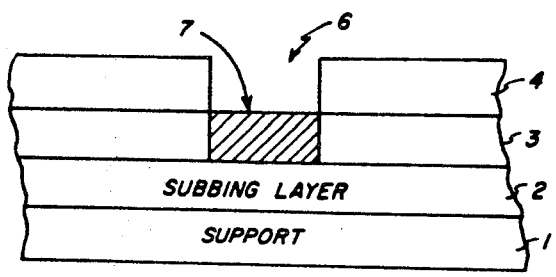
FIG. 3 illustrates schematically a dye imbibition imaging element after imagewise exposure, development and imbibing at least one dye into the mordant layer of the element.
Figure 3A:
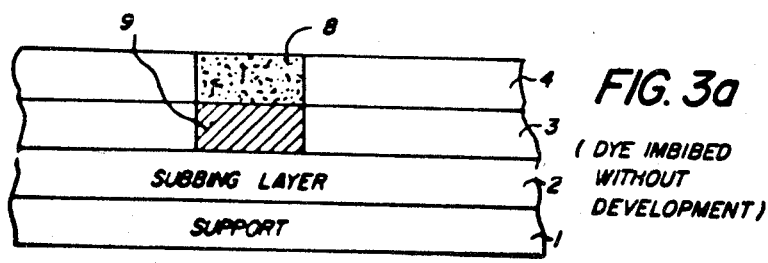
FIG. 3a illustrates schematically a dye imbibition imaging element after imagewise exposure and imbibing at least one dye into the mordant layer of the element without the need of development to remove at least part of the unexposed area of the photohardenable layer.

After development of the element of FIG. 2 by water rinsing and then imbibing a dye into the element, an element is formed as illustrated in FIG. 3. Dye according to this embodiment is imbibed through area 6 of photohardenable polyesterionomer layer 4 into area 7 of mordant layer 3. The area 6 of layer 4 in FIG. 3 in an alternative embodiment is not removed, but rather is sufficiently permeable and unhardened after exposure of layer 4 to permit the desired concentration of dye to pass into the mordant layer. This alternative embodiment is illustrated in FIG. 3A. The unhardened area 8 of FIG. 3A is not removed by development. Rather, in this alternative, dye is imbibed through area 8 of layer 4 into area 9 of mordant layer 3.

The following examples will further illustrate the invention.

EXAMPLE 1

Element of the Invention

A dye imbibition imaging element for producing a positive, continuous tone, dye image was prepared as illustrated in FIG. 1 of the drawings.

A mordant layer was coated on a gelatin subbed poly(ethylene terephthalate) film product. The mordant layer consisted of:

| Component | Coverage mg/ft$^2$ | mg/dm$^2$ |
|---|---|---|
| poly(styrene-co-N—vinyl-benzyl-N,N—dimethyl-N—cyclohexylammonium chloride-co-divinylbenzene) (49:49:2) (mordant) | 40 | 4.3 |
| gelatin (binder) | 20 | 2.2 |
| formaldehyde (hardener) | 2 | 0.22 |
| surfactant (Surfactant 10G, which is para-isononylphenoxypolyglycidol and is a trademark and available from the Olin Corporation, U.S.A.). | 1.2 | 0.13 |

The following water-soluble photohardenable polyesterionomer layer was coated on the mordant layer:

| Component | Coverage mg/ft$^2$ | mg/dm$^2$ |
|---|---|---|
| poly[1,4-cyclohexylenebis-(oxyethylene)succinate-co-phenylenebis(acrylate)-co-5-(4-sodiosulfophenoxy)isophthalate (15:55:30)] (polyesterionomer) | 54 | 5.83 |
| 3-(7-methoxy-3-coumarinoyl)-1-methylpyridinium p-toluenesulfonate (sensitizer) | 2.7 | 0.29 |

The resulting imaging element was imagewise exposed by means of a conventional photographic step tablet for 78 seconds and by means of a mercury vapor light source (Kalvar Kalkard 200 exposing unit, which is a tradename of and available from the Kalvar Company, United States).

The following processing steps were then carried out:
(1) 30-second rinse of the exposed element by means of running distilled water;
(2) brief swabbing by means of a cotton pad wet with distilled water;
(3) 60-second immersion in a 0.4 percent aqueous solution of cyan dye (the dye was D1 from Table II in a pH 10.0 buffer); and
(4) 20-second rinse by means of running tap water.

Figure 4:
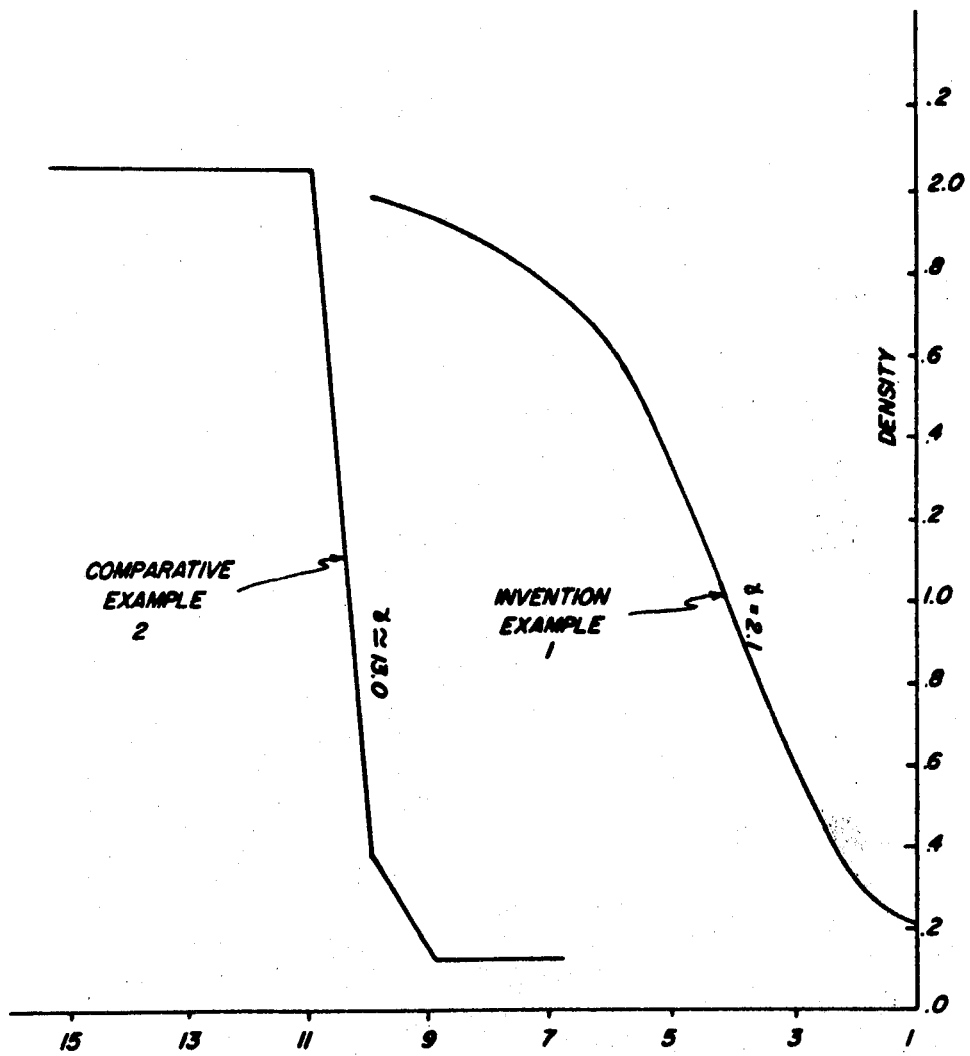
FIG. 4 illustrates density versus exposure curves for an element according to the invention illustrated in following Example 1, compared to an element according to comparative Example 2.

Each of the processing steps was carried out at room temperature (about 21° C.). A continuous tone image was produced having a gamma of 2.1 read by reflection to red light while in contact with a white paper print stock. This is illustrated in FIG. 4 of the drawings.

EXAMPLE 2

Element Without Polyesterionomer

This is a comparative example.

The procedure described in Example 1 was repeated, with the exception that the following cyclohexanone soluble composition was coated on the mordant layer:

| Component | Coverage mg/ft$^2$ | mg/dm$^2$ |
|---|---|---|
| poly[1,4-cyclohexylenebis-(oxyethylene)succinate-co-p-phenylenebis(acrylate) (45:55) | 54 | 5.83 |
| sensitizer of Example 1 | 2.7 | 0.29 |

The element was imagewise exposed as described in Example 1. The following processing steps were then carried out at 21° C.:
(1) 30-second immersion in cyclohexanone;
(2) a brief, light swabbing by means of a cotton pad wet with cyclohexanone;
(3) 60-second immersion in a 0.4 percent by weight aqueous solution of cyan dye as in Example 1; and
(4) 20-second rinse by means of running tap water.

A high contrast image was produced having a gamma of about 13.0 measured as described in Example 1. This is illustrated in FIG. 4 of the drawings.

EXAMPLE 3

Element Without Polyesterionomer

This is a comparative example.

Figure 5:
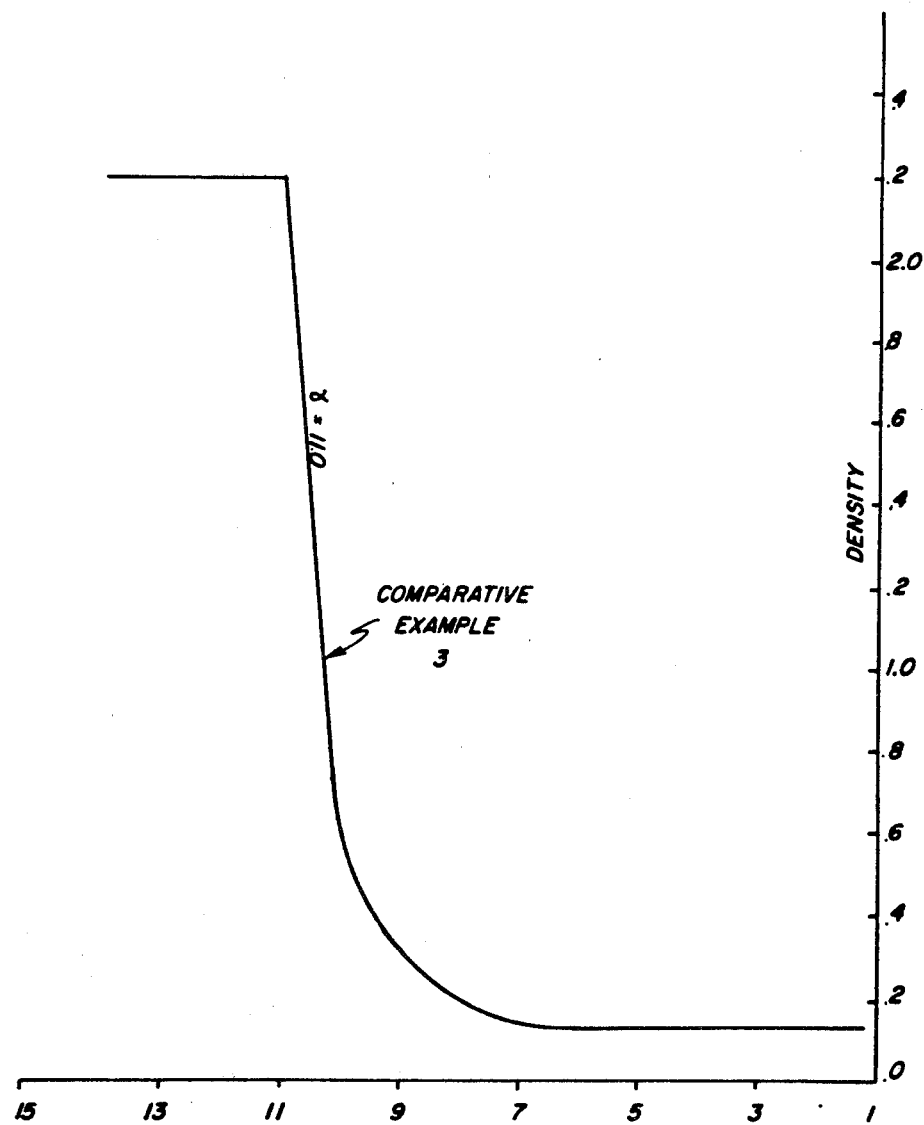
FIG. 5 illustrates a density versus exposure curve for an element according to comparative Example 3 demonstrating that the element of comparative Example 3 provides an image that has undesirably high contrast.

The procedure described in Example 2 was repeated, with the exception that processing was carried out directly by immersing the exposed element for three minutes at 21° C. in a 0.4 percent Acid Fuchsin dye solution comprising as the solvent one part by volume distilled water to nine parts by volume acetone. The element was then briefly rinsed in distilled water. A high contrast dye image was produced having a gamma of about 11.0 measured as described in Example 1. This is illustrated in FIG. 5 of the drawings.

EXAMPLE 4

Element Containing Photoresist

This is a comparative example.

An imaging element was prepared by coating a mordant layer as described in Example 1 on a gelatin subbed poly(ethylene terephthalate) film support. A photoresist layer was then coated on the mordant layer. The photoresist layer was coated by means of a solution comprising 7.67 ml of Kodak Photo Resist, a tradename of and available from Eastman Kodak Company, United States. (Example 1 of U.S. Pat. No. 3,255,002 describes the use of Kodak Photo Resist) diluted by means of 25 ml of 2-methoxy ethyl acetate on the mordant layer at a wet coating coverage of 0.25 ml/dm$^2$. The element was permitted to dry.

The element was imagewise exposed by means of a conventional photographic step tablet for 96 seconds and by means of a mercury vapor light source (Kalvar Kalkard 200 exposing unit). The following processing steps were then carried out at 21° C.:
(1) 60-second immersion (with agitation) in a developer comprising two parts by volume 2-methoxy ethyl acetate and eight parts by volume xylene;

(2) 60-second immersion in a 0.4 percent by weight aqueous solution of Acid Fuchsin dye; and
(3) brief rinse with distilled water.

Figure 6:
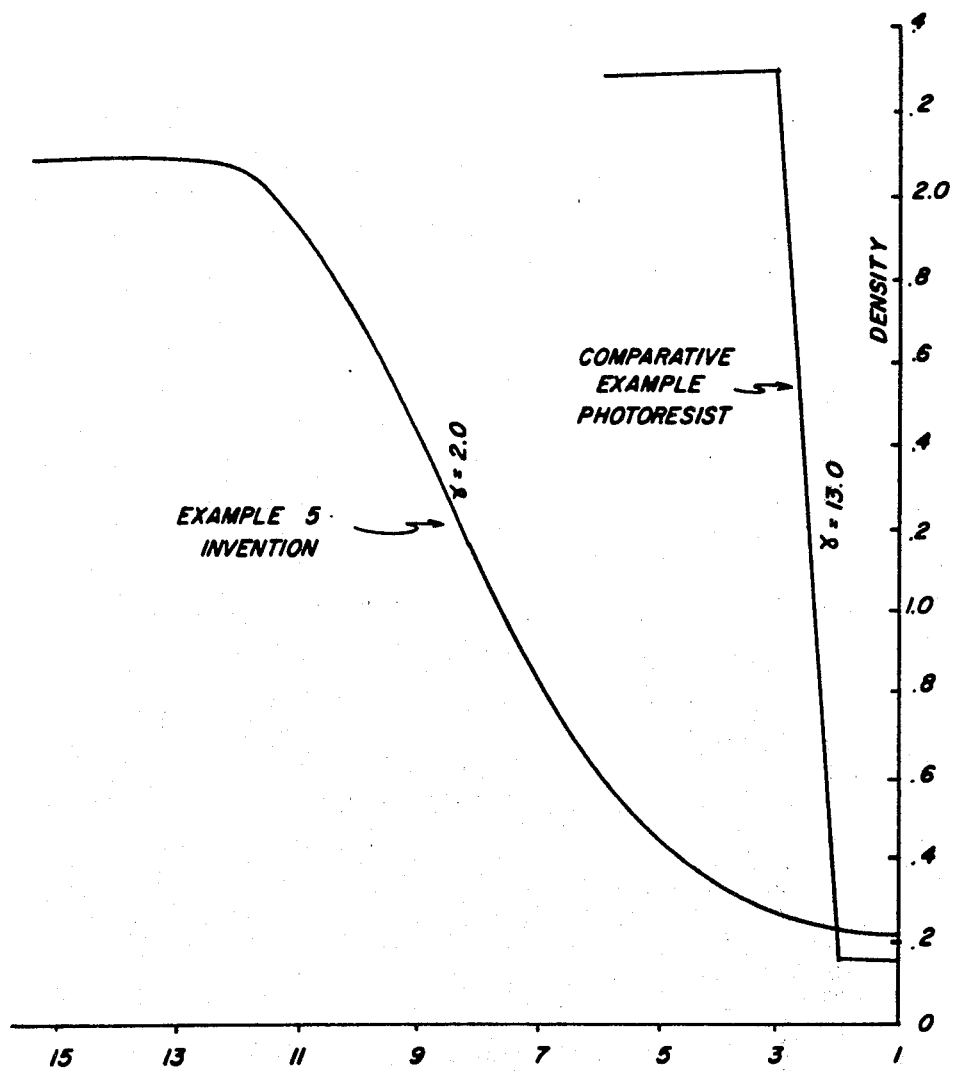
FIG. 6 illustrates density versus exposure curves for an element according to the invention illustrated in following Example 4, compared to an element according to comparative Example 5 comprising a photoresist.

A high contrast image was produced having a gamma of 13.0 read by reflection to green light while in contact with a white paper print stock. This is illustrated in FIG. 6 of the drawings.

EXAMPLE 5

Element of Invention

The imaging element of Example 1 was imagewise exposed, as described in Example 4. The exposed element was processed as described in Example 1 at 21° C. and with Acid Fuchsin as the dye. A continuous tone image was produced having a gamma of 2.0. This is illustrated in FIG. 6.

EXAMPLE 6

An imaging element was prepared as described in Example 1. The element was imagewise exposed as described in Example 1 and then processed at 21° C. as follows:
(1) 60-second immersion in a 0.4 percent by weight aqueous solution of Acid Fuchsin dye; and
(2) 20-second rinse by means of running tap water.

Figure 7:
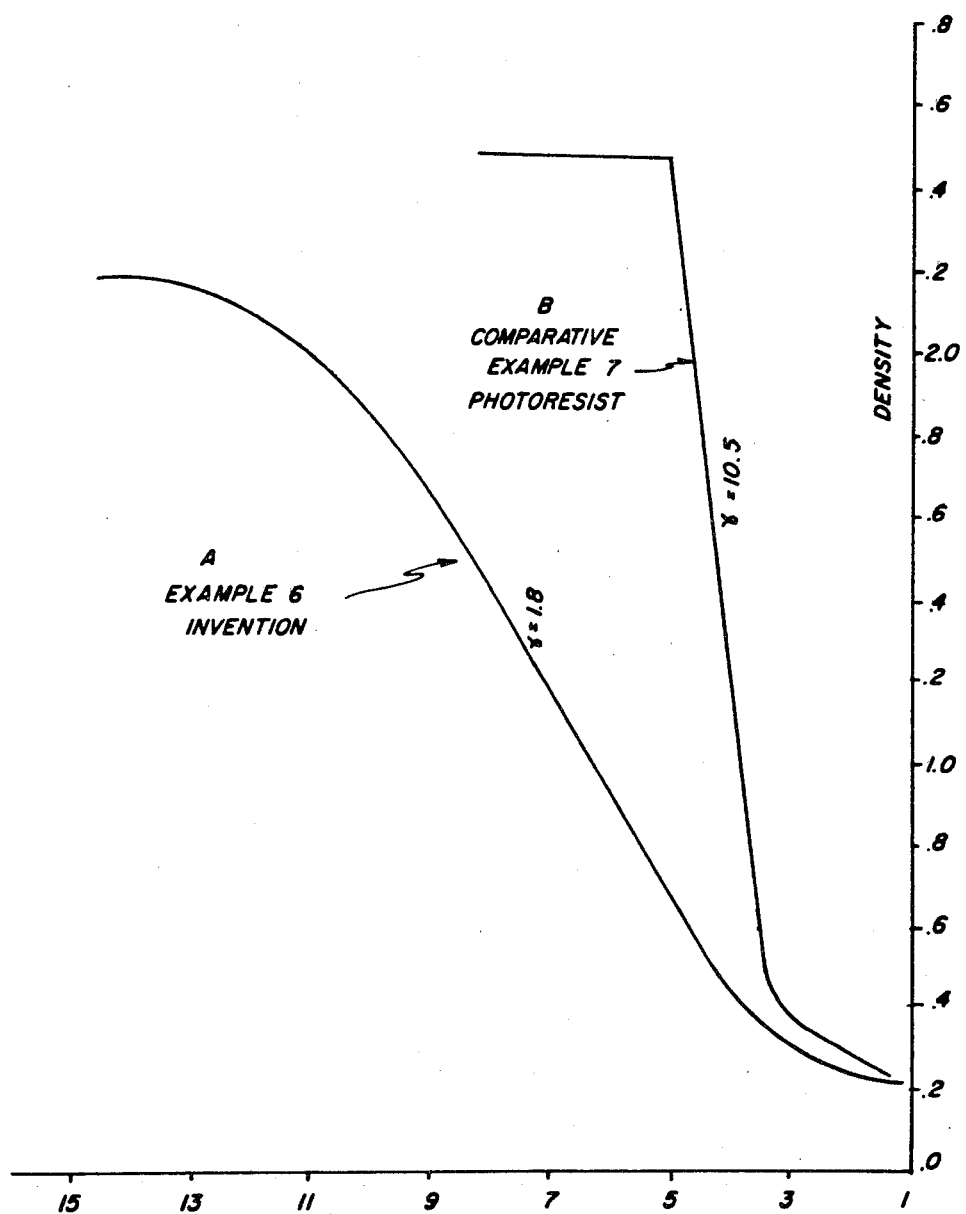
FIG. 7 illustrates density versus exposure curves for an element according to the invention illustrated in following Example 6, compared to an element according to comparative Example 7 comprising a photoresist.

A continuous tone image was produced having a gamma of 1.8. The results of the example are illustrated by the curve A in FIG. 7 of the drawings.

EXAMPLE 7

This is a comparative example.

An element was prepared as described in Example 4. The element was imagewise exposed as described in Example 4 and then processed at 21° C. as follows:
(1) 60-second immersion with agitation in a 0.4 percent Acid Fuchsin dye solution comprising one part by volume water and nine parts by volume 2-methoxy ethyl acetate; and
(2) a brief rinse in distilled water.

A high contrast image was produced having a gamma of 10.5. This is illustrated by curve B in FIG. 7 of the drawings.

EXAMPLE 8

Useful results were obtained in an element according to the invention comprising poly[1,4-cyclohexylenebis-(oxyethylene) succinate-co-p-phenylenebis(acrylate)-co-3,3'-sodioiminodisulfonyldibenzoate] (25:60:15) as the photosensitive polyesterionomer. The element was imagewise exposed and processed similar to the exposure and processing in Example 1.

EXAMPLE 9

Useful results were obtained in an element according to the invention comprising poly[1,4-cyclohexylenebis-(oxyethylene) succinate-co-p-phenylenebis(acrylate)-co-5-sodiosulfoisophthalate] (20:60:20) as the photosensitive polyesterionomer. The element was imagewise exposed and processed similar to the exposure and processing in Example 1.

EXAMPLE 10

Useful results were obtained in an element according to the invention comprising poly[1,4-cyclohexylenebis-(oxyethylene)succinate-co-p-phenylenebis(acrylate)-co-5-(4-sodiosulfocyclohexyloxy)-1,3-cyclohexanedicarboxylate] (15:55:30) as the photosensitive polyesterionomer. The element was imagewise exposed and processed similar to the exposure and processing in Example 1.

EXAMPLES 11 THROUGH 13

Useful results were obtained in an element according to Example 1 with one of the following sensitizers in place of the sensitizer described in Example 1:

| Example No. | Sensitizer |
| --- | --- |
| 11 | CH$_3$O—⟨structure⟩—N(CH$_3$)⊕ FSO$_3$⊖ |
| 12 | CH$_3$O—⟨structure⟩—N(CH$_3$)⊕ BF$_4$⊖ |
| 13 | CH$_3$O—⟨structure⟩—N(CH$_3$)⊕ ZnCl$_3$⊖ |

Other sensitizers are also useful in an element according to the invention. Other useful sensitizers are described in, for example, U.S. Pat. No. 4,147,552.

EXAMPLE 14

Three-Color Overlay Proof According to the Invention

Imaging elements like that of Example 1 were imagewise exposed to red, green and blue continuous tone separation positives respectively for 54 seconds by means of a pulsed Xenon light source (NuArc Platemaker exposing unit). Processing was accomplished as follows:
(1) 30-second rinse by means of running distilled water;
(2) a brief swabbing by means of a cotton pad wet with distilled water;
(3) 60-second immersion in a 0.4 percent by weight aqueous solution of dye; and
(4) 20-second rinse by means of running tap water.

An element was prepared and the process was repeated to prepare a red separation positive, a green separation positive and a blue separation positive. The cyan dye for the red separation positive was the described dye D1 in Table II. The magenta dye for the green separation positive was a dye represented by the formula:

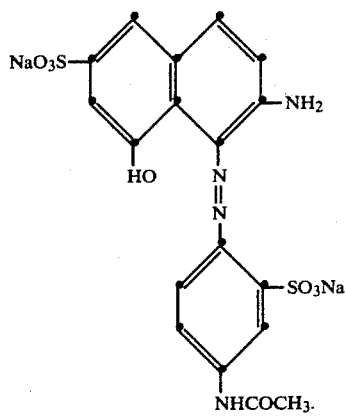

The yellow dye for the blue separation positive was a dye represented by the formula:

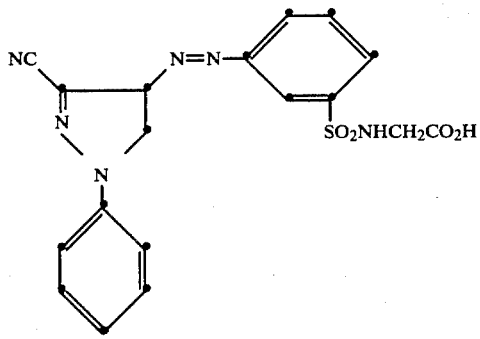

All dye baths were prepared at 0.4 percent by weight dye using pH 10.0 buffer solution.

The resulting dyed positives were overlayed in register, producing a good quality, continuous tone proof.

The invention has been described in detail with particular reference to preferred embodiments thereof, but it will be understood that variations and modifications can be effected within the spirit and scope of the invention.

What is claimed is:

1. In a dye imbibition imaging element comprising, in sequence:

(a) a support having thereon, (b) a cationic mordant layer for an anionic dye, and (c) a sensitized photohardenable photopolymer layer superposed on said mordant layer, the improvement wherein:

said photopolymer layer consists essentially of a photosensitive polyesterionomer represented by the formula:

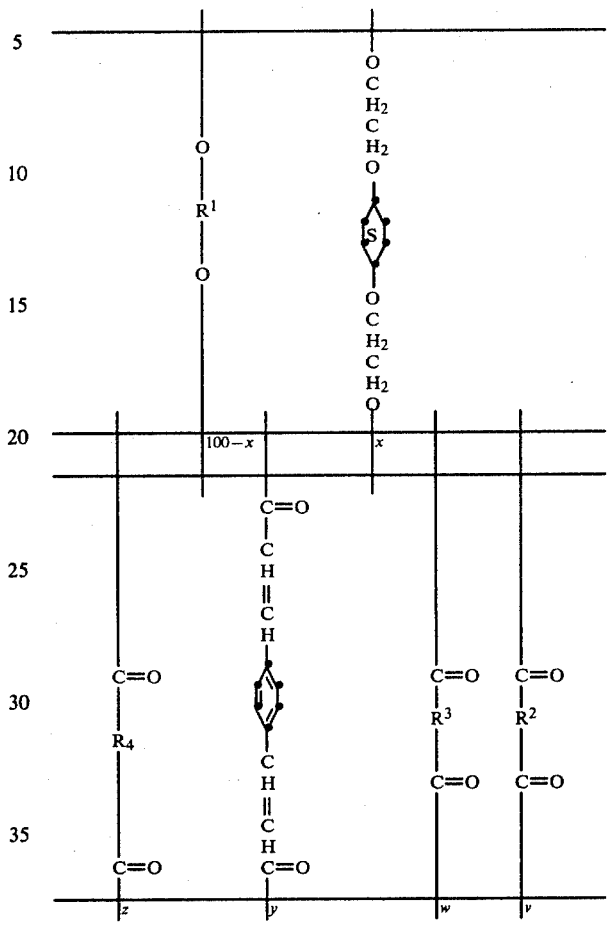

wherein:

$R^1$ is straight or branched chain alkylene containing 2 to 10 carbon atoms, cycloalkylene containing 5 or 6 carbon atoms, or an aliphatic ether group containing 3 to 12 carbon atoms;

$R^2$ is an aromatic group containing 6 to 12 carbon atoms;

$R^3$ is straight or branched chain alkylene containing 2 to 10 carbon atoms;

$R^4$ is an ionic group selected from those having the structures:

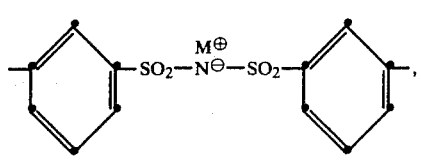

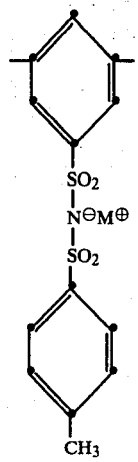

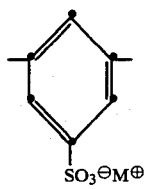, and

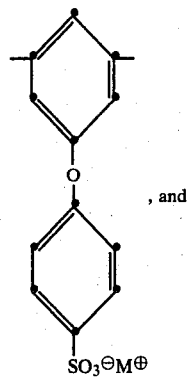

$M^\oplus$ is an alkali metal or ammonium ion;
x is 50 to 100 mole percent;
v is 0 to 35 mole percent;
w is 0 to 35 mole percent;
y is 50 to 85 mole percent; and
z is 15 to 40 mole percent.

2. A dye imbibition imaging element as in claim 1 wherein said polyesterionomer consists essentially of poly[1,4-cyclohexylenebis(oxyethylene) succinate-co-p-phenylenebis(acrylate)-co-5-sodiosulfoisophthalate].

3. A dye imbibition imaging element as in claim 1 wherein said polyesterionomer consists essentially of poly[1,4-cyclohexylenebis(oxyethylene) succinate-co-p-phenylenebis(acrylate)-co-5-(4-sodiosulfophenoxy)-iso-phthalate].

4. A dye imbibition imaging element as in claim 1 wherein said polyesterionomer consists essentially of poly[1,4-cyclohexylenebis(oxyethylene) succinate-co-p-phenylenebis(acrylate)-co-3,3'-sodioiminodisulfonyl-dibenzoate].

5. A dye imbibition imaging element as in claim 1 wherein said polyesterionomer consists essentially of poly[1,4-cyclohexylenebis(oxyethylene)succinate-co-p-phenylenebis(acrylate)-co-5-(4-sodiosulfocyclohexyloxy)-1,3-cyclohexanedicarboxylate].

6. A dye imbibition imaging element as in claim 1 wherein said mordant consists essentially of a protonated polyvinylimidazole.

7. A dye imbibition imaging element as in claim 1 wherein said mordant consists essentially of a polymer having a repeating unit represented by the formula:

wherein:
T is an organo group and is a portion of a polymer backbone;
Q is a chemical bond or chemical group linking $Z^\oplus$ to T;
$X^\ominus$ is an acid anion; and
$Z^\oplus$ is a cationic group.

8. A dye imbibition imaging element as in claim 1 wherein said mordant consists essentially of a polymer having a repeating unit represented by the formula:

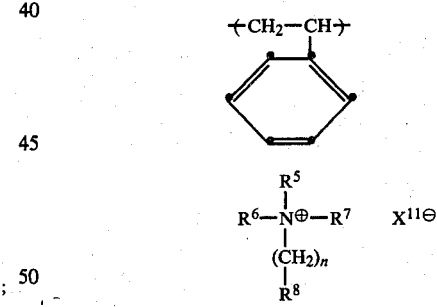

wherein:
$R^5$ is alkylene containing 1 to 3 carbon atoms;
$R^6$ and $R^7$ are the same or different and each is aryl, aralkyl or alkaryl containing 6 to 20 carbon atoms, or alkyl containing 1 to 10 carbon atoms;
n is 0, 1 or 2;
$R^8$ is methyl or phenyl; and
$X^{11\ominus}$ is an acid anion.

9. A dye imbibition imaging element as in claim 1 also comprising gelatin in said mordant layer.

10. A dye imbibition imaging element comprising a support having thereon:
(a) a cationic mordant layer consisting essentially of poly[styrene-co-N-vinylbenzyl-N,N-dimethyl-N-cyclohexylammonium chloride-co-divinylbenzene (49:49:2)], having superposed thereon;

(b) a sensitized photohardenable photopolymer layer consisting essentially of poly[1,4-cyclohexylenebis-(oxyethylene) succinate-co-p-phenylenebis(acrylate)-co-5-sodiosulfoisophthalate].

11. A dye imbibition imaging element comprising a support having thereon:
(a) a cationic mordant layer consisting essentially of poly[styrene-co-N-vinylbenzyl-N,N-dimethyl-N-cyclohexylammonium chloride-co-divinylbenzene (49:49:2)] having superposed thereon:
(b) a sensitized photohardenable photopolymer layer consisting essentially of poly[1,4-cyclohexylenebis-(oxyethylene) succinate-co-p-phenylenebis(acrylate)-co-5-(4-sodiosulfophenoxy)-isophthalate].

12. A dye imbibition imaging element comprising a support having thereon:
(a) a cationic mordant layer consisting essentially of poly[styrene-co-N-vinylbenzyl-N,N-dimethyl-N-cyclohexylammonium chloride-co-divinylbenzene (49:49:2)] having superposed thereon:
(b) a sensitized photohardenable photopolymer layer consisting essentially of poly[1,4-cyclohexylenebis-(oxyethylene) succinate-co-p-phenylenebis(acrylate)-co-3,3'-sodioiminodisulfonyldibenzoate].

13. A dye imbibition imaging element comprising a support having thereon:
(a) a cationic mordant layer consisting essentially of poly[styrene-co-N-vinylbenzyl-N,N-dimethyl-N-cyclohexylammonium chloride-co-divinylbenzene (49:49:2)] having superposed thereon:
(b) a sensitized photohardenable photopolymer layer consisting essentially of poly[1,4-cyclohexylenebis-(oxyethylene)succinate-co-p-phenylenebis(acrylate)-co-5-(4-sodiosulfocyclohexyloxy)-1,3-cyclohexanedicarboxylate].

14. A dye imbibition element as in claim 1 also comprising in said mordant layer a gelatino binder.

15. A dye imbibition element as in claim 1 also comprising in said mordant layer a gelatino binder and a hardener.

16. a process for formation of a positive, continuous tone, dye image in a dye imbibition imaging element comprising, in sequence:
(a) a support having thereon,
(b) a cationic mordant layer consisting essentially of poly[styrene-co-N-vinylbenzyl-N,N-dimethyl-N-cyclohexylammonium chloride-co-divinylbenzene (49:49:2)], having superposed thereon:
(c) a sensitized photohardenable photopolymer layer consisting essentially of photosensitive poly[1,4-cyclohexylenebis(oxyethylene)succinate-co-p-phenylenebis(acrylate)-co-5-sodiosulfoisophthalate];
said process comprising the steps of:
(1) imagewise exposing said photopolymer layer to activating radiation to imagewise harden the photopolymer layer;
(2) developing said photopolymer layer by water rinsing the photopolymer layer; and then
(3) imbibing an anionic dye into said mordant layer through the unexposed areas of said photopolymer layer.

17. A process for formation of a positive, continuous tone, dye image in a dye imbibition imaging element comprising, in sequence;
(a) a support having thereon,
(b) a cationic mordant layer consisting essentially of poly[styrene-co-N-vinylbenzyl-N,N-dimethyl-N-cyclohexylammonium chloride-co-divinylbenzene (49:49:2)] having superposed thereon:
(c) a sensitized photohardenable photopolymer layer consisting essentially of photosensitive poly[1,4-cyclohexylenebis(oxyethylene) succinate-co-p-phenylenebis(acrylate)-co-5-(4-sodiosulfophenoxy)-isophthalate],
said process comprising the steps of:
(1) imagewise exposing said photopolymer layer to activating radiation to imagewise harden the photopolymer layer;
(2) developing said photopolymer layer by water rinsing the photopolymer layer; and then
(3) imbibing an anionic dye into said mordant layer through the unexposed areas of said photopolymer layer.

18. A process for formation of a positive, continuous tone, dye image in a dye imbibition imaging element comprising, in sequence:
(a) a support having thereon,
(b) a cationic mordant layer consisting essentially of poly[styrene-co-N-vinylbenzyl-N,N-dimethyl-N-cyclohexylammonium chloride-co-divinylbenzene (49:49:2)] having superposed thereon:
(c) a sensitized photohardenable photopolymer layer consisting essentially of photosensitive poly[1,4-cyclohexylenebis(oxyethylene) succinate-co-p-phenylenebis(acrylate)-co-3,3'-sodioiminodisulfonyldibenzoate],
said process comprising the steps of:
(1) imagewise exposing said photopolymer layer to activating radiation to imagewise harden the photopolymer layer;
(2) developing said photopolymer layer by water rinsing the photopolymer layer; and then
(3) imbibing an anionic dye into said mordant layer through the unexposed areas of said photopolymer layer.

19. A process for forming a positive, continuous tone, dye image in a dye imbibition imaging element comprising, in sequence:
(a) a support having thereon,
(b) a cationic mordant layer consisting essentially of poly[styrene-co-N-vinylbenzyl-N,N-dimethyl-N-cyclohexylammonium chloride-co-divinylbenzene (49:49:2)] having superposed thereon;
(c) a sensitized photohardenable photopolymer layer consisting essentially of poly[1,4-cyclohexylenebis-(oxyethylene)succinate-co-p-phenylenebis(acrylate)-co-5-(4-sodiosulfocyclohexyloxy)-1,3-cyclohexanedicarboxylate];
said process comprising the steps of:
(1) imagewise exposing said photopolymer layer to activating radiation to imagewise harden the photopolymer layer; and then
(2) imbibing at least one anionic dye through the unexposed areas of the photopolymer layer into the cationic mordant layer.

20. A process for formation of a continuous tone, dye image in a receiver layer comprising a first cationic mordant of a predetermined mordanting strength; said process comprising the steps of:
(a) imagewise exposing a sender element comprising:
(i) a support having thereon:
(ii) a mordant layer consisting essentially of a second cationic mordant for an anionic dye, said second cationic mordant having a lesser mordanting strength than the first cationic mordant, and having superposed thereon:

(iii) a sensitized photohardenable, photopolymer layer consisting essentially of a photosensitive polyesterionomer represented by the formula:

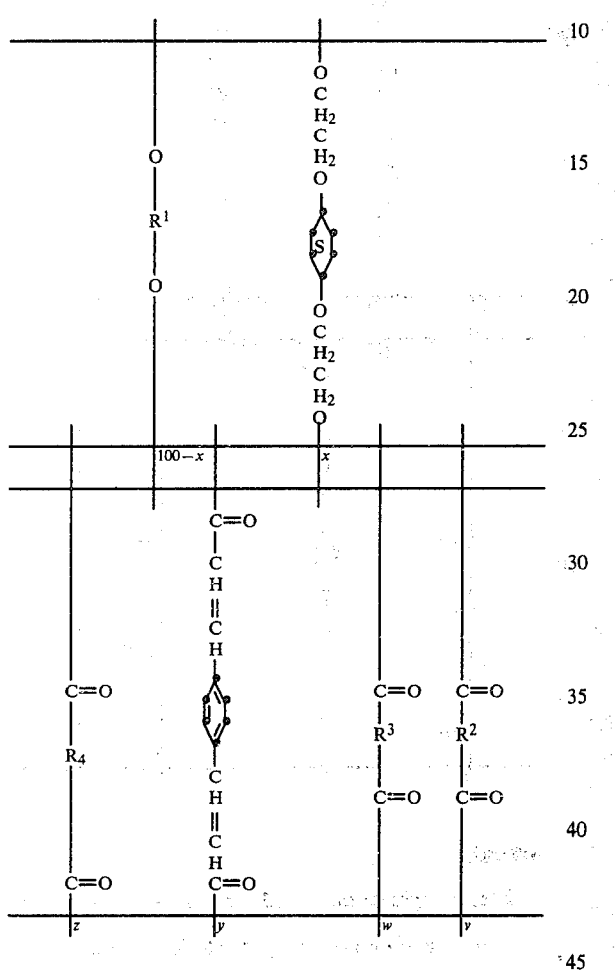

wherein:

$R^1$ is straight or branched chain alkylene containing 2 to 10 carbon atoms, cycloalkylene containing 5 or 6 carbon atoms, or an aliphatic ether group containing 3 to 12 carbon atoms;

$R^2$ is an aromatic group containing 6 to 12 carbon atoms;

$R^3$ is straight or branched chain alkylene containing 2 to 10 carbon atoms;

$R^4$ is an ionic group selected from those having the structures:

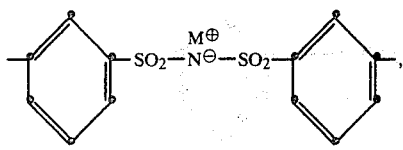

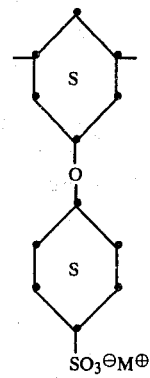

$M^\oplus$ is an alkali metal or ammonium ion;
x is 50 to 100 mole percent;
v is 0 to 35 mole percent;
w is 0 to 35 mole percent;
y is 50 to 85 mole percent; and
z is 15 to 40 mole percent; to imagewise harden said photopolymer layer;

(b) developing said photopolymer layer by means of water by rinsing the photopolymer layer to form hardened image areas in the photopolymer layer;

(c) imbibing at least one anionic dye into the second cationic mordant layer, said dye being temporarily immobilized in the portions of the second cationic mordant corresponding to unexposed portions of said photopolymer layer; and, (d) imagewise transferring said anionic dye to said receiver layer by contacting the receiver layer with the side of the sender element containing the second cationic mordant in the presence of an aqueous solution that aids transfer of the anionic dye into the first cationic mordant.

21. A process as in claim 20 wherein said imagewise transferring is carried out at a temperature within the range of about 15° C. to about 40° C.

22. A process as in claim 20 also comprising in (b) removing unexposed portions of the photopolymer layer by water rinsing.

23. A process for formation of a continuous tone, dye image in a receiver layer comprising a first cationic mordant of a predetermined mordanting strength; said process comprising the steps of:

(a) imagewise exposing a sender element comprising:
(i) a support having thereon:
(ii) a mordant layer consisting essentially of a second cationic mordant consisting essentially of poly[styrene-co-N-vinylbenzyl-N,N-dimethyl-N-cyclohexylammonium chloride-co-divinylbenzene (49:49:2)] and having superposed thereon,
(iii) a sensitized photohardenable, photopolymer layer consisting essentially of poly[1,4-cyclohexylenebis(oxyethylene) succinate-co-p-phenylenebis(acrylate)-co-5-(4-sodiosulfophenoxy)-isophthalate] to imagewise harden said photopolymer layer;

(b) developing said photopolymer layer by water rinsing the photopolymer layer to remove unhardened areas in the photopolymer layer;

(c) imbibing at least one anionic dye into the second cationic mordant layer, said dye being temporarily immobilized in the portions of the second cationic mordant corresponding to unexposed portions of said photopolymer layer; and (d) imagewise transferring said anionic dye to said receiver layer by contacting the receiver layer with the side of the sender element containing the second cationic mordant in the presence of an aqueous solution that aids transfer of the anionic dye into the first cationic mordant.

24. A process for forming a positive, continuous tone, dye image in a dye imbibition imaging element comprising, in sequence:
(a) a support having thereon,
(b) a cationic mordant layer for an anionic dye; and
(c) a sensitized, photohardenable photopolymer layer comprising a photosensitive polyesterionomer represented by the formula:

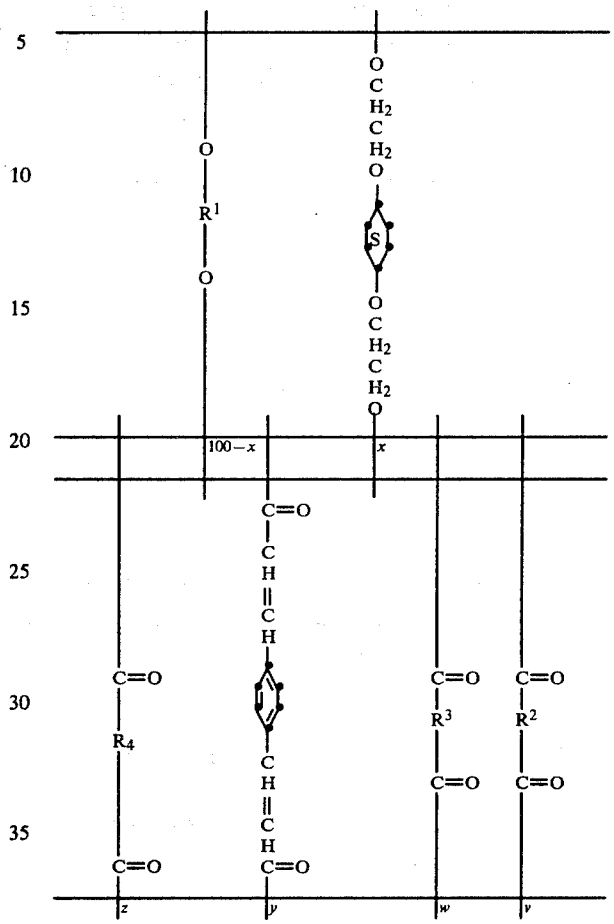

wherein:

$R^1$ is straight or branched chain alkylene containing 2 to 10 carbon atoms, cycloalkylene containing 5 or 6 carbon atoms, or an aliphatic ether group containing 3 to 12 carbon atoms;

$R^2$ is an aromatic group containing 6 to 12 carbon atoms;

$R^3$ is straight or branched chain alkylene containing 2 to 10 carbon atoms;

$R^4$ is an ionic group selected from those having the structure:

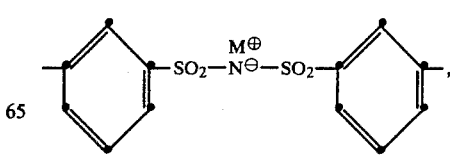

-continued

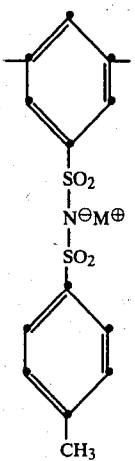

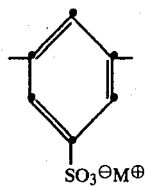

, and

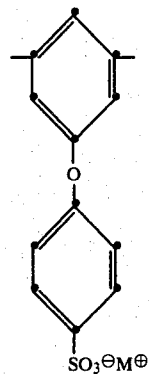

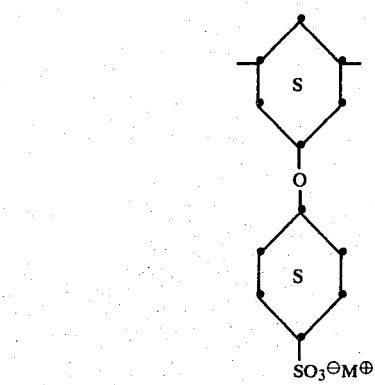

$M^\oplus$ is an alkali metal or ammonium ion;
x is 50 to 100 mole percent;
v is 0 to 35 mole percent;
w is 0 to 35 mole percent;
y is 50 to 85 mole percent; and
z is 15 to 40 mole percent,
superposed on said mordant layer; said process comprising the steps of:

(1) imagewise exposing said photopolymer layer to activating radiation to imagewise harden the photopolymer layer;

(2) developing said photopolymer layer by water rinsing the photopolymer layer; and, then (3) imbibing an anionic dye into said mordant layer through unexposed areas of said photopolymer layer.

25. A process for forming a positive, continuous tone, dye image in a dye imbibition imaging element comprising, in sequence:

(a) a support having thereon, (b) a cationic mordant layer for an anionic dye, and (c) a sensitized, photohardenable photopolymer layer comprising a photosensitive polyesterionomer represented by the formula:

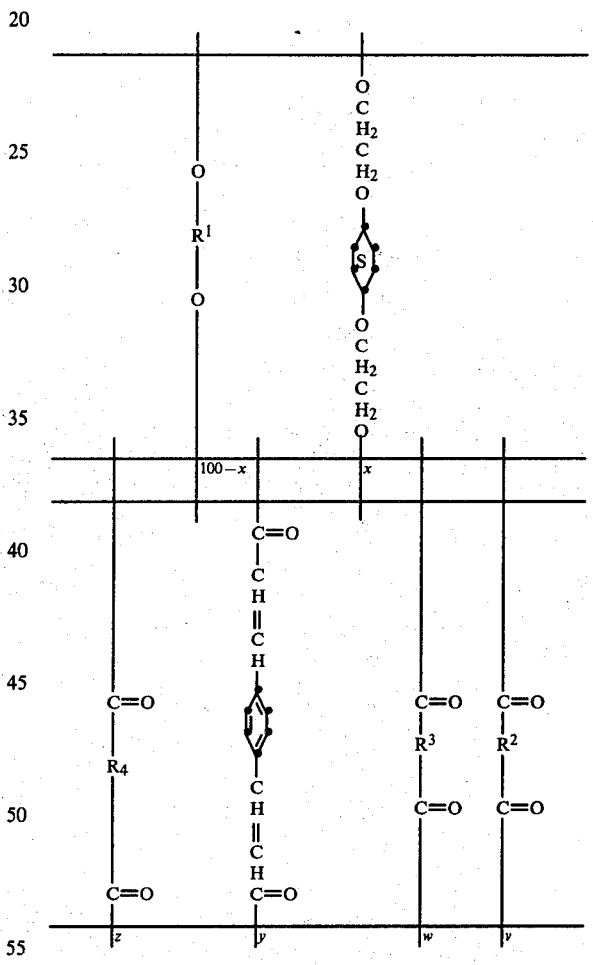

wherein:

$R^1$ is straight or branched chain alkylene containing 2 to 10 carbon atoms, cycloalkylene containing 5 or 6 carbon atoms, or an aliphatic ether group containing 3 to 12 carbon atoms;

$R^2$ is an aromatic group containing 6 to 12 carbon atoms;

$R^3$ is straight or branched chain alkylene containing 2 to 10 carbon atoms;

$R^4$ is an ionic group selected from those having the structure:

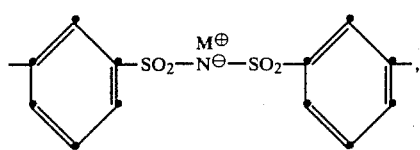

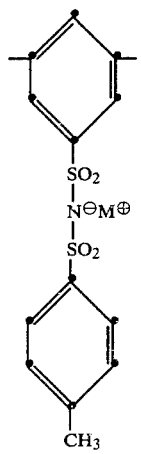

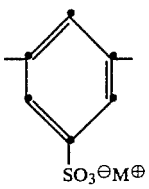

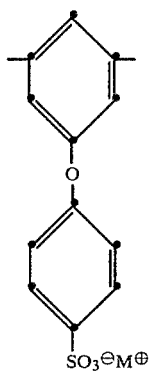

, and

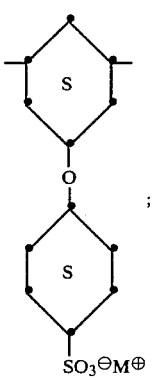

;

M⊕ is an alkali metal or ammonium ion;
x is 50 to 100 mole percent;
v is 0 to 35 mole percent;

w is 0 to 35 mole percent;
y is 50 to 85 mole percent; and
z is 15 to 40 mole percent;
said process comprising the steps of:
(1) imagewise exposing said photopolymer layer to activating radiation to imagewise harden the photopolymer layer; and then
(2) imbibing at least one anionic dye through the unexposed areas of the photopolymer layer into the cationic mordant layer.

26. A process for forming a positive, continuous tone, dye image in a receiver layer comprising a first cationic mordant of a predetermined mordanting strength comprising the steps:
(a) imagewise exposing a sender element comprising:
(i) a support having thereon:
(ii) a mordant layer comprising a second mordant having a lesser mordanting strength than the first cationic mordant, and having thereon and contiguous to the mordant layer:
(iii) a sensitized, photohardenable, photopolymer layer consisting essentially of a photosensitive polyesterionomer represented by the formula:

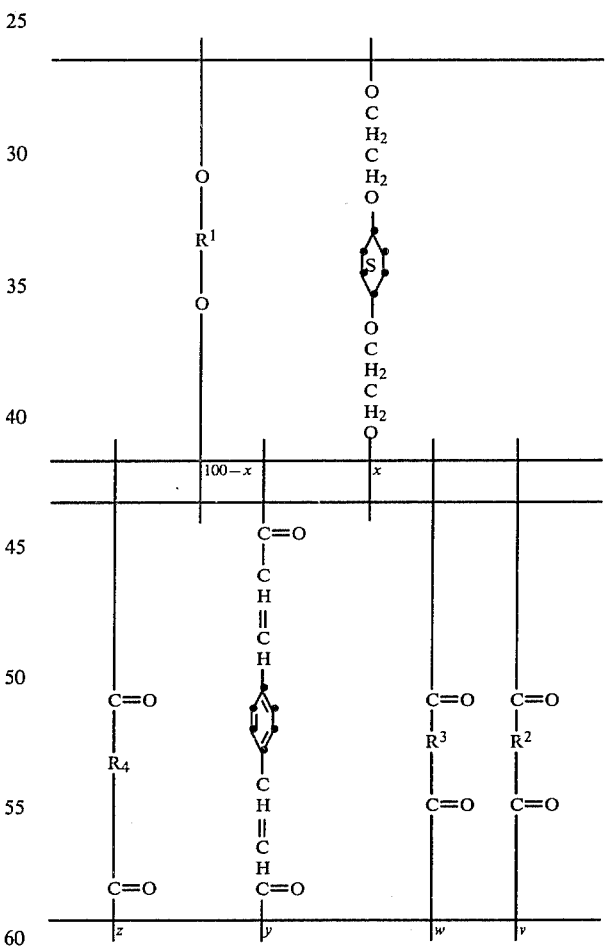

wherein:
$R^1$ is straight or branched chain alkylene containing 2 to 10 carbon atoms, cycloalkylene containing 5 or 6 carbon atoms, or an aliphatic ether group containing 3 to 12 carbon atoms;
$R^2$ is an aromatic group containing 6 to 12 carbon atoms;

$R^3$ is straight or branched chain alkylene containing 2 to 10 carbon atoms;

$R^4$ is an ionic group selected from those having the structure:

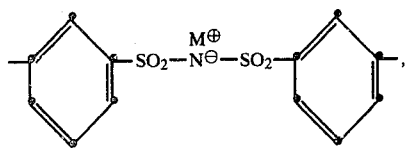

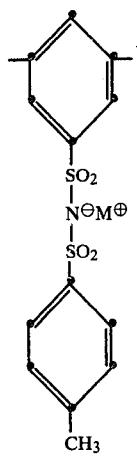

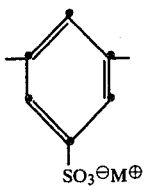

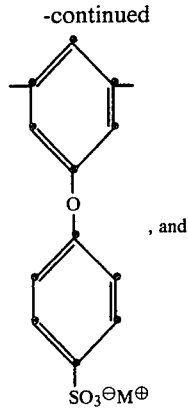

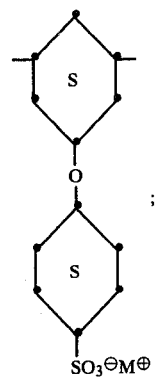

$M^\oplus$ is an alkali metal or ammonium ion;
x is 50 to 100 mole percent;
v is 0 to 35 mole percent;
w is 0 to 35 mole percent;
y is 50 to 85 mole percent; and
z is 15 to 40 mole percent, to imagewise harden the photopolymer layer;

(b) imbibing at least one anionic dye through the unexposed areas of the photopolymer layer into the second cationic mordant layer without the need of removing portions of the photopolymer layer; and then (c) imagewise transferring the anionic dye from the second cationic mordant layer, through unexposed areas of the photopolymer layer into the receiver layer in the presence of an aqueous solution which aids transfer of the anionic dye.

* * * * *